(12) United States Patent
Mieda et al.

(10) Patent No.: US 10,556,974 B2
(45) Date of Patent: Feb. 11, 2020

(54) CURABLE AND HYGROSCOPIC RESIN COMPOSITION FOR SEALING ELECTRONIC DEVICES, SEALING RESIN, AND ELECTRONIC DEVICE

(71) Applicant: FURUKAWA ELECTRIC CO., LTD., Tokyo (JP)

(72) Inventors: Tetsuya Mieda, Tokyo (JP); Takumi Asanuma, Tokyo (JP); Yasushi Ishizaka, Tokyo (JP)

(73) Assignee: FURUKAWA ELECTRIC CO., LTD., Tokyo (JP)

( * ) Notice: Subject to any disclaimer, the term of this patent is extended or adjusted under 35 U.S.C. 154(b) by 157 days.

(21) Appl. No.: 15/663,371

(22) Filed: Jul. 28, 2017

(65) Prior Publication Data

US 2017/0327608 A1 Nov. 16, 2017

Related U.S. Application Data (63) Continuation of application No. PCT/JP2015/086529, filed on Dec. 28, 2015.

(30) Foreign Application Priority Data

Jan. 30, 2015 (JP) .................................. 2015-017221

(51) Int. Cl.
| | |
|---|---|
| *C07F 5/06* | (2006.01) |
| *C07F 7/00* | (2006.01) |
| *C08F 20/06* | (2006.01) |
| *C08F 20/18* | (2006.01) |
| *C08F 2/48* | (2006.01) |

(52) U.S. Cl.
CPC .............. *C08F 20/18* (2013.01); *C07F 5/069* (2013.01); *C07F 7/003* (2013.01); *C08F 20/06* (2013.01); *C08F 2/48* (2013.01); *C08F 2500/02* (2013.01)

(58) Field of Classification Search
CPC .... B01J 20/223; B01J 20/261; B01J 2220/44; C07F 5/069; C08F 2/44; C08F 20/18; C08F 290/02; C08F 290/048; C08F 2/48; C08F 2500/02; H01L 51/5253; H01L 51/448
See application file for complete search history.

(56) References Cited

U.S. PATENT DOCUMENTS

| | | |
|---|---|---|
| 2005/0227114 A1 | 10/2005 | Tanaka et al. |
| 2008/0289750 A1 | 11/2008 | Kanai et al. |
| 2009/0045729 A1 | 2/2009 | Fujita et al. |
| 2009/0250166 A1* | 10/2009 | Pachl ........................ C08F 2/48 156/308.2 |
| 2010/0089636 A1 | 4/2010 | Ramadas et al. |
| 2010/0148160 A1 | 6/2010 | Cao |
| 2012/0042694 A1 | 2/2012 | Brown et al. |
| 2014/0305582 A1 | 10/2014 | Ogawa et al. |

FOREIGN PATENT DOCUMENTS

| | | |
|---|---|---|
| CN | 100503030 C | 6/2009 |
| CN | 101518151 A | 8/2009 |
| CN | 101743779 A | 6/2010 |
| CN | 101747860 A | 6/2010 |
| CN | 102983085 A | 3/2013 |
| JP | 2000-169752 A | 6/2000 |
| JP | 2008-95039 A | 4/2008 |
| JP | 2008-166244 A | 7/2008 |
| JP | 2010-528407 A | 8/2010 |
| JP | 2011-42712 A | 3/2011 |
| JP | 2012-38660 A | 2/2012 |
| JP | 5062648 B2 | 10/2012 |
| JP | 5213303 B2 | 6/2013 |
| JP | 2013-216782 A | 10/2013 |
| JP | 2013-545826 A | 12/2013 |
| WO | WO 2006/107748 A1 | 10/2006 |
| WO | WO 2013/168629 A1 | 11/2013 |
| WO | WO 2014/062135 A1 | 4/2014 |

OTHER PUBLICATIONS

JP2000-169752 machine translation downloaded Feb. 27, 2019.*
International Search Report for PCT/JP2015/086529 (PCT/ISA/210) dated Mar. 8, 2016.
Written Opinion of the International Searching Authority for PCT/JP2015/086529 (PCT/ISA/237) dated Mar. 8, 2016.
Chinese Office Action and Search Report, dated Jun. 22, 2018, for corresponding Chinese Application No. 201580048535.9, with an English translation of the Office Action.

* cited by examiner

*Primary Examiner* — Irina S Zemel
*Assistant Examiner* — Jeffrey S Lenihan
(74) *Attorney, Agent, or Firm* — Birch, Stewart, Kolasch & Birch, LLP (57) ABSTRACT

A curable and hygroscopic resin composition for sealing electronic devices, having at least a (meth)acrylate oligomer (a) having the number-average molecular weight of 1,500 to 5,000, a low molecular weight (meth)acrylate (b) having an average molecular weight of 170 to 500, a moisture-reactive organometallic compound (c), and a polymerization initiator (d), wherein the (meth)acrylate oligomer (a) and the low molecular weight (meth)acrylate (b) are multifunctional (meth)acrylates in which the number of (meth)acryloyl groups is from 1.5 to 3 in one molecule of each of the (meth)acrylate oligomer (a) and the low molecular weight (meth)acrylate (b); a sealing resin; and an electronic device.

6 Claims, 1 Drawing Sheet

CURABLE AND HYGROSCOPIC RESIN COMPOSITION FOR SEALING ELECTRONIC DEVICES, SEALING RESIN, AND ELECTRONIC DEVICE

CROSS-REFERENCE TO RELATED APPLICATIONS

This application is a Continuation of PCT International Application No. PCT/JP2015/086529 filed on Dec. 28, 2015, which claims priority under 35 U.S.C. § 119 (a) to Japanese Patent Application No. 2015-017221 filed in Japan on Jan. 30, 2015. Each of the above applications is hereby expressly incorporated by reference, in its entirety, into the present application.

TECHNICAL FIELD

The present invention relates to a curable and hygroscopic resin composition for sealing electronic devices, which is capable of forming a hygroscopic layer having high waterproofness and flexibility, a sealing resin, and an electronic device sealed with the foregoing resin composition. In particular, the present invention relates to bond or seal of an organic electronic device, an organic light-emitting diode element, a touch panel, a light-emitting diode (LED), and a solar cell.

BACKGROUND ART

The organic light-emitting diode element (hereinafter, also referred to as OLED element) has a problem with a gradual deterioration of the emission property, such as emission brightness and emission efficiency caused by the use thereof. Examples of the causes include organic matter denaturation and electrode oxidation, due to penetration of moisture or the like into the organic light-emitting diode element.

In order to prevent these problems, a technique for suppressing deterioration of the organic light-emitting diode element has been studied, by sealing the organic light-emitting diode element, thereby preventing moisture or the like from penetrating into the organic light-emitting diode element (see, for example, Patent Literature 1).

However, this technique needs a space for placing a getter for water removal as a sealing cover, and therefore has a problem with making it thinner. In order to solve this problem, a technique has been studied, which enables to making it thinner by blending a desiccant filler in a radiation curable resin (see, for example, Patent Literature 2).

However, regarding the sealant in which the desiccant filler is blended like the above-described technique, light permeability becomes low, because light is shield by the filler. This sealant can be used to seal the so-called bottom emission-type device in which an organic light-emitting layer is formed on a transparent substrate and light is taken out from the transparent substrate side. However, this sealant is not suitable for sealing the so-called top emission-type device in which sealing is performed so as to cover the upper portion of the organic light-emitting layer formed on a substrate and light is taken out from the sealed side. Further, in the case of using inorganic particles as a desiccant, there is a high risk that the inorganic particles themselves crush and destruct the OLED element under the pressure at the time of sealing. Further, in the case of using a water absorptive polymer, water absorption ability thereof is not enough.

In order to solve these problems, a technique has also been studied, which adds a moisture-reactive organometallic compound to a sealing resin (see, for example, Patent Literatures 3 to 5). In the case of adding an organometallic compound to the sealing resin, it is also required to make the organometallic compound and the sealing resin homogeneously compatible and to suppress migration of alcohol which is released from the organometallic compound.

However, in the technique which has been studied in the past in order to satisfy these requirements, it was necessary to make a degree of cross-linkage of the sealant cured material low, for example, by using a non-crosslinked material or a monoacrylate. As the result, a water vapor barrier property of these sealants was poor, and also flexibility thereof was not enough, and therefore bendability was not enough.

CITATION LIST

Patent Literatures

Patent Literature 1: JP-T-2010-528407 ("JP-T" means published searched patent publication)
Patent Literature 2: WO 2006/107748 A1
Patent Literature 3: Japanese Patent No. 5062648
Patent Literature 4: JP-A-2012-38660 ("JP-A" means unexamined published Japanese patent application)
Patent Literature 5: Japanese Patent No. 5213303

SUMMARY OF INVENTION

Technical Problem

In recent years, for a practical use of the organic light-emitting diode element, a higher water vapor barrier property is required. Further, as for a substrate material of the organic light-emitting diode element, a need for adoption of not only a glass plate and a metal plate, but also a resin film having bendability or an ultrathin glass film, is increasing. For such an intended use, a sealing resin is required, which bends moving on with the substrate, and which therefore does not break away.

However, as for the sealing resin according to the conventional art, a low crosslinking density is required as mentioned above, and therefore the conventional sealing resin is not enough to satisfy a high water vapor barrier property, flexibility, and bending resistance.

Further, for not only the sealant but also the adhesive in general, it is often practiced to lower a viscosity by adding a diluent, thereby improving workability at the time of sealing. However, in the case where compatibility between the diluent and the resin is not good, a transparent resin becomes cloudy due to addition of the diluent. The cloudy sealant can be used to seal the so-called bottom emission-type device. However, the composition which becomes cloudy due to a mixing with the transparent resin, is not suitable for a sealant, because it becomes difficult to keep a water vapor barrier property. Presumably, this is caused because a mixed resin forms a so-called sea-island structure and light is diffusely reflected at the interface thereof to become cloudy, and moisture becomes easy to penetrate from the formed interface.

More specifically, the present invention addresses the provision of a curable and hygroscopic resin composition for sealing electronic devices, which is capable of obtaining a sealing resin having a higher water vapor barrier property than a conventional sealant, without migration, due to a good compatibility between materials which constitute the curable and hygroscopic resin composition for sealing electronic devices (hereinafter, also referred to simply as a constituent material), despite a high crosslinking density.

Further, the present invention addresses the provision of a curable and hygroscopic resin composition for sealing electronic devices, which is capable of obtaining a sealing resin having satisfactory flexibility and bendability enough to bend by moving on with the substrate and not to break away, even when a resin film having bendability, an ultrathin glass film, or a metal foil is used for a substrate material of the organic light-emitting diode device.

Further, the present invention addresses the provision of a curable and hygroscopic resin composition for sealing electronic devices, having a resin viscosity which is excellent in workability at the time of applying it to a substrate.

Further, the present invention addresses the provision of a sealing resin and an electronic device, each of which exhibits excellent sealing performance as the result of sealing with the curable and hygroscopic resin composition for sealing electronic devices of the present invention, and each of which also exhibits excellent flexibility and lightweight property, when a resin film having bendability or an ultrathin glass film is used for a substrate.

Solution to Problem

The inventors of the present invention have intensively studied so that the problems facing the above-described conventional art can be solved, by incorporating a large molecular weight (meth)acryl oligomer, a low molecular weight (meth)acrylate, a moisture-reactive organometallic compound, and a polymerization initiator, in a curable and hygroscopic resin composition for sealing electronic devices.

As a result, it is found that a crosslinking density can be regulated, by setting the molecular weight and the number of acryloyl groups of each of the (meth)acryl oligomer and the low molecular weight (meth)acrylate to a particular ranges, thereby to make the resin composition excellent in terms of bendability, a water vapor barrier property and a resin viscosity. Further, compatibility between constituent materials is also good, so that a moisture-reactive organometallic compound which has the effect of increasing hydrophobicity on the substrate surface does not cause a phase separation. As a result, it is found that a high water vapor barrier property can be achieved, by a synergy effect between a water absorption effect due to a moisture-reactive organometallic compound and hydrophobization of the substrate surface.

Further, it is found that the electronic device sealed with the above-described curable and hygroscopic resin composition for sealing electronic devices, is excellent in sealing performance, and is excellent in flexibility and lightweight property, when a resin film having bendability or an ultrathin glass film is used for a substrate.

That is, the present invention provides the following means:

(1) A curable and hygroscopic resin composition for sealing electronic devices, comprising at least a (meth)acrylate oligomer (a) having the number-average molecular weight of 1,500 to 5,000, a low molecular weight (meth)acrylate (b) having an average molecular weight of 170 to 500, a moisture-reactive organometallic compound (c), and a polymerization initiator (d),
wherein the (meth)acrylate oligomer (a) and the low molecular weight (meth)acrylate (b) are multifunctional (meth)acrylates in which the number of (meth)acryloyl groups is from 1.5 to 3 in one molecule of each of the (meth)acrylate oligomer (a) and the low molecular weight (meth)acrylate (b).

(2) The curable and hygroscopic resin composition for sealing electronic devices described in the item (1), wherein a moisture permeability of a cured film having a thickness of 100 µm, which has been formed by curing a composition in which the moisture-reactive organometallic compound (c) is removed from the curable and hygroscopic resin composition for sealing electronic devices, is 10 g/m$^2$/24-hr or less under the condition of 40° C. and 90% relative humidity.

(3) The curable and hygroscopic resin composition for sealing electronic devices described in the item (1) or (2), wherein from 5 to 30 mass % of the (meth)acrylate oligomer (a), from 40 to 90 mass % of the low molecular weight (meth)acrylate (b), and from 5 to 30 mass % of the moisture-reactive organometallic compound (c) are contained at this rate.

(4) The curable and hygroscopic resin composition for sealing electronic devices described in any one of the items (1) to (3), wherein the moisture-reactive organometallic compound (c) has at least one ligand having an acetylacetonato coordinating group and at least one alkoxide ligand.

(5) A sealing resin, formed by shaping the curable and hygroscopic resin composition for sealing electronic devices described in any one of the items (1) to (4) into a film, and curing the film.

(6) An electronic device, sealed with the curable and hygroscopic resin composition for sealing electronic devices described in any one of the items (1) to (4), or having the sealing resin described in the item (5).

In the present invention, the numerical range expressed by using the expression "to" means a range including numerical values before and after the expression "to" as the lower limit and the upper limit.

Further, the term "(meth)acrylate" may be any of a methacrylate and an acrylate, and is used as a collective term. Accordingly, this term includes either one of a methacrylate and an acrylate, and a mixture thereof.

Herein, the (meth)acrylate includes a (meth)acrylic acid ester, a (meth)acrylic acid, and a (meth)acrylic acid salt.

Note that, generally the (meth)acryloyl group is also referred to as a (meth)acrylate group.

Advantageous Effects of Invention

According to the curable and hygroscopic resin composition for sealing electronic devices of the present invention, a sealing resin having a higher water vapor barrier property than a conventional sealant can be obtained, without migration, by virtue of a good compatibility between constituent materials, despite a high crosslinking density.

Further, a sealing resin, which can be obtained by using the curable and hygroscopic resin composition for sealing electronic devices of the present invention, has flexibility and bendability enough to bend moving on with the substrate and not to break away, even when a resin film having bendability or an ultrathin glass film is used for a substrate material of the organic light-emitting diode device.

Further, the curable and hygroscopic resin composition for sealing electronic devices of the present invention has a low resin viscosity, which is excellent in workability at the time of applying it on a substrate.

In addition, a sealing resin and an electronic device, each of which has been sealed with the curable and hygroscopic resin composition for sealing electronic devices of the present invention, are excellent in a sealing performance, and are excellent in flexibility and lightweight property, when a resin film having bendability or an ultrathin glass film is used for a substrate.

Other and further features and advantages of the invention will appear more fully from the following description, appropriately referring to the accompanying drawings.

MODE FOR CARRYING OUT THE INVENTION

Hereinafter, a usage embodiment of the curable and hygroscopic resin composition for sealing electronic devices of the present invention (hereinafter, also referred to simply as a sealing resin composition), is described in detail with reference to figures. Note that, the usage embodiment of the present invention is not limited thereto.

Figure 1:
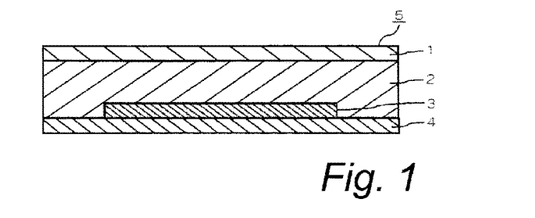
FIG. 1 is a schematic cross-sectional view showing one embodiment in which an organic light-emitting diode element is sealed with the curable and hygroscopic resin composition for sealing electronic devices of the present invention.

The curable and hygroscopic resin composition for sealing electronic devices of the present invention is used to seal an organic light-emitting diode element 3 in an organic light-emitting diode device 5, as shown in FIG. 1. More specifically, the curable and hygroscopic resin composition for sealing electronic devices is provided as a sealing resin 2 between elements for any of organic electronic devices, such as an organic light-emitting diode element 3 provided on an element substrate 4, and a sealing substrate 1. In this way, the organic light-emitting diode element 3 is tightly sealed with the element substrate 4 and the sealing substrate 1, so that any of various kinds of organic electronic devices, such as an organic light-emitting diode device 5 having a solid adhesion sealing structure is obtained. Examples of the organic electronic devices include an organic electroluminescence display (organic EL display), an organic electroluminescence lighting (organic EL lighting), an organic semiconductor, and an organic solar cell. Note that, as is apparent from the above, the sealing resin 2 means a resin formed by curing the sealing resin composition of the present invention.

<<Curable and Hygroscopic Resin Composition for Sealing Electronic Eevices>>

The curable and hygroscopic resin composition for sealing electronic devices of the present invention is a curable and hygroscopic resin composition for sealing electronic devices, comprising at least a (meth)acrylate oligomer (a) having the number-average molecular weight of 1,500 to 5,000, a low molecular weight (meth)acrylate (b) having an average molecular weight of 170 to 500, a moisture-reactive organometallic compound (c), and a polymerization initiator (d), in which the (meth)acrylate oligomer (a) and the low molecular weight (meth)acrylate (b) are such multifunctional (meth)acrylates in which the number of (meth)acryloyl groups is from 1.5 to 3 in one molecule of each of the (meth)acrylate oligomer (a) and the low molecular weight (meth)acrylate (b).

<(Meth)acrylate oligomer (a)>

The (meth)acrylate oligomer (a) in the present invention is an oligomer containing a (meth)acryl group in its basic resin.

As for the basic resin, use may be made of any one of general elastic resins. In particular, unsaturated and saturated aliphatic hydrocarbon polymers or the like are preferred.

Examples of the unsaturated aliphatic hydrocarbon polymers include polybutadiene, polyisoprene, polyisobutylene, and the like. Examples of the aliphatic hydrocarbons polymers include polypropylene, polyethylene, hydrogenated compounds (hydrogen-added compound) of the above-described unsaturated aliphatic hydrocarbon polymers, and the like. Examples of hetero-element-containing hydrocarbons include polyurethane, polyester, and the like.

Further, in the present invention, the basic resin includes partially hydrogen-added compounds of the above-described basic resins in addition to the hydrogen-added compounds described as the afore-mentioned aliphatic hydrocarbons.

The (meth)acryloyl group may be contained in any of a main chain, a side chain, and an end of the basic resin, but it is preferably contained in the end of the basic resin.

Further, the (meth)acryloyl group may be bonded to the basic resin through the intermediary of a bond, such as a urethane bond or an ester bond.

If the molecular weight of the (meth)acrylate oligomer (a) in the present invention is too low, the viscosity of the sealing resin composition becomes too low, and as a result, acquaintanceship with a sealing substrate becomes good, which results in sealing-working friendly. However, if the molecular weight thereof is too low, a crosslinked density of the sealing resin becomes too high, and modulus of elasticity is made too high, and therefore peeling-off at the sealed corner portion is made high.

On the other hand, if the (meth)acrylate oligomer (a) becomes a too high molecular weight, a bendability of the sealing resin composition after cured is improved. However, a viscosity of the sealing resin composition before curing is made high, so that application onto a sealing substrate becomes difficult.

The number-average molecular weight of the (meth)acrylate oligomer (a) in the present invention is from 1,500 to 5,000.

From the view point of being excellent in flexibility, the number-average molecular weight is preferably 2,000 or more, and more preferably 3,000 or more. Further, from the view point of being excellent in compatibility to the low molecular weight (meth)acrylate (b), the number-average molecular weight is preferably 4,000 or less, and more preferably 3,500 or less.

Note that, the number-average molecular weight is a value calculated by subjecting a 1% solution obtained by dissolving it in tetrahydrofuran to gel permission chromatography (GPC equipment: GPC system manufactured by Waters Corporation, column: "TSKgel GMHHR-N" manufactured by Tosoh Corporation, flow rate: 1.0 mL/min), and then converting the measured value into the polystyrene conversion number-average molecular weight.

The (meth)acrylate oligomer (a) in the present invention is such a multifunctional (meth)acrylate oligomer that from 1.5 to 3 of (meth)acryloyl groups are contained in one molecule thereof.

Although the number of (meth)acryloyl groups is from 1.5 to 3, the number of 2 to 3 is preferred and the number of 2 is more preferred.

In this regard, as for the (meth)acrylate oligomer (a) in which one and a half (meth)acryloyl groups are contained, examples thereof include: an equimolar mixture of a (meth)acrylate oligomer in which one (meth)acryloyl group is contained in one molecule thereof and another (meth)acrylate oligomer in which two (meth)acryloyl groups are contained in one molecule thereof.

The number of (meth)acryloyl groups in one molecule of the (meth)acrylate oligomer (a) can be obtained by estimating a structure and a molecular weight from IR measurement, $^1$H-NMR measurement, thermal decomposition GC/MS measurement, or GPC measurement, each of which is commonly practiced.

As for the (meth)acrylate oligomer (a), a commercially available product may be purchased and used.

Examples thereof include: TEAI-1000 and TE-2000 (each trade name) which are an urethane di(meth)acrylate resin having a polybutadiene or a hydrogenated polybutadiene at its end and EMA-3000 (trade name) which is a methacrylate resin having a polybutadiene at its end, each of which is manufactured by Nippon Soda Co., Ltd.; CN307, CN308, and CN309 (each trade name), each of which is a hydrophobic acrylate oligomer and CN310 and CN9104 (each trade name), each of which is a hydrophobic aliphatic urethane acrylate, each of which is manufactured by SARTOMER Inc.; and BAC-45 (trade name) which is a diacrylate having a polybutadiene at its end and SPBDA-S30 (trade name) which is a diacrylate having a hydrogenated polybutadiene at its end, each of which is manufactured by Osaka Organic Chemical Industry Ltd.

In the present invention, a resin whose main chain is a polybutadiene or a hydrogenated polybutadiene is preferred, and in addition to this resin, a resin having a urethane di(meth)acrylate at both ends is more preferred.

Further, as for the (meth)acrylate oligomer (a), use may be also made of a compound, which is synthesized by reacting a basic resin (aa) having a reactive group, such as a hydroxyl group or the like, and a compound (ab) having both a functional group which reacts with the reactive group, and an acryloyl group.

Herein, the basic resin (aa) having a reactive group, such as a hydroxyl group or the like, has preferably from 1.5 to 3 reactive groups, more preferably from 2 to 3 reactive groups, and still more preferably 2 reactive groups, as is the case in the (meth)acrylate oligomer (a).

Herein, the number of (meth)acryloyl groups in one molecule of the (meth)acrylate oligomer (a) can be calculated from a blended ratio of a compound (ab) having both a functional group which reacts with the reactive group and a (meth)acryloyl group, to the reactive group of a basic resin (aa) having a reactive group, such as a hydroxyl group or the like.

For example, in the case where 2 moles of 2-isocyanatoethyl acrylate are reacted with 1 mole of a basic resin (aa) having 2 hydroxyl groups in one molecule in this rate, and all of the hydroxyl group and the isocyanate group completely react with each other, the obtained (meth)acrylate oligomer (a) has 2 acryloyl groups in one molecule.

Note that, the number of (meth)acryloyl groups can be also calculated by the above-described measurement method.

Examples of the reactive group in the basic resin (aa) and the functional group in the compound (ab) include a hydroxyl group, a carboxyl group, an amino group, a mercapto group, a cyclic acid anhydride group, an epoxy group, an isocyanate group (—N═C═O), and the like.

Herein, in the case where one of the reactive group in the basic resin (aa) and the functional group in the compound (ab) is a hydroxyl group, a carboxyl group, an amino group, a mercapto group, or a cyclic acid anhydride group, examples of the other group include an epoxy group and an isocyanate group. In the case where one group is a cyclic acid anhydride group, examples of the other group include a hydroxyl group, a carboxyl group, an amino group, and a mercapto group. Note that, in the case where one group is an epoxy group, the other group may be an epoxy group, and further in the case where one group is a carboxyl group, the other group may be a hydroxyl group, an amino group, or a mercapto group.

As for the reactive group in the basic resin (aa), a hydroxyl group, a carboxyl group, and a mercapto group are preferred, and a hydroxyl group is particularly preferred.

Examples of the basic resin (aa) include a multifunctional oligomer. In particular, an oligomer modified by functional groups at both ends is preferred. As for the oligomer, the above-described preferable basic resins of the (meth)acrylate oligomer (a) are preferred. As for the reactive group, the above-described preferable reactive groups are preferred.

As for the basic resin (aa), a commercially available product may be purchased and used.

Examples thereof include: KRASOL HLBH-P2000 and KRASOL HLBH-P3000 (each trade name), each of which is a hydrogenated polyolefin having a hydroxyl group at its end (a hydrogenated polybutadiene having a hydroxyl group at its end) manufactured by Cray Valley; EPOL (trade name) which is a polyolefin having a hydroxyl group at its end, manufactured by Idemitsu Kosan Co., Ltd.; Poly bd R-15HT and Poly bd R-45HT (each trade name), each of which is a polybutadiene having a hydroxyl group at its end, and Poly ip (trade name) which is a polyisoprene having a hydroxyl group at its end; GI-1000, GI-2000, and GI-3000 (each trade name), each of which is a hydrogenated polybutadiene having hydroxyl groups at its both ends and each of which is manufactured by Nippon Soda Co., Ltd.; and POLYTALE (trade name) which is a polyhydroxypolyolefin oligomer manufactured by Mitsubishi Chemical Corporation.

In the present invention, the basic resin (aa) is preferably a hydrogenated polybutadiene having hydroxyl groups at its both ends or a polybutadiene having hydroxyl groups at its both ends (preferably the number-average molecular weight of 1,500 to 4,000), and more preferably a hydrogenated polybutadiene having hydroxyl groups at its both ends.

As for the functional group of the compound (ab), an isocyanate group and an epoxy group are preferred, and an isocyanate group is more preferred.

Examples of the compound (ab) include a (meth)acrylic acid ester having an isocyanate group in an alcohol moiety thereof. In particular, a (meth)acrylic acid alkyl ester substituted with an isocyanate group is preferred. Examples of such a compound include 2-isocyanatoethyl methacrylate and 2-isocyanatoethyl acrylate.

Further, examples of the preferable compound having a functional group other than an isocyanate group include a (meth)acrylic monomer having the functional group.

As for the compound (ab), a commercially available product may be purchased and used.

Examples of the product include KARENZ AOI (manufactured by Showa Denko K.K., 2-isocyanatoethyl acrylate) and KARENZ MOI (manufactured by Showa Denko K.K., 2-isocyanatoethyl methacrylate).

<Low molecular weight (meth)acrylate (b)>

The low molecular weight (meth)acrylate (b) in the present invention generally has a low viscosity, and when used in combination with the (meth)acrylate oligomer (a), has the effect of lowering a viscosity of the sealing resin composition and enhancing a crosslinking density of the sealing resin after cured thereby to enhance a water vapor barrier property.

However, if the molecular weight is low, the elastic modulus of the sealing resin becomes high, which results in lowering of flexibility. On the other hand, if the molecular weight is high, the crosslinking density of the sealing resin is not enough, which results in lowering of water vapor barrier property.

The average molecular weight (hereinafter, also referred to simply as a molecular weight) of the low molecular weight (meth)acrylate (b) in the present invention is from 170 to 500.

From the viewpoint of being well balanced with flexibility, the molecular weight is preferably 200 or more, and more preferably 300 or more. Further, from the viewpoint of being excellent in a water vapor barrier property, the molecular weight is preferably 400 or less, and more preferably 350 or less.

Note that, the average molecular weight means a molecular weight or the number-average molecular weight measured by gel permeation chromatography.

The low molecular weight (meth)acrylate (b) in the present invention is such a multifunctional low molecular weight (meth)acrylate that from 1.5 to 3 of (meth)acryloyl groups are contained in one molecule thereof.

Although the number of (meth)acryloyl groups is from 1.5 to 3, the number of 2 to 3 is preferred, and the number of 2 is more preferred.

In this regard, as for the low molecular weight (meth) acrylate (b) in which one and a half (meth)acryloyl groups are contained, examples thereof include an equimolar mixture of a low molecular weight (meth)acrylate (b) in which one (meth)acryloyl group is contained in one molecule thereof and a low molecular weight (meth)acrylate (b) in which two (meth)acryloyl groups are contained in one molecule thereof.

As for the low molecular weight (meth)acrylate (b), a commercially available product may be purchased and used.

Examples thereof include: ETHYLENE DIACRYLATE (molecular weight 170) and TRIETHYLENE GLYCOL DIMETHACRYLATE (molecular weight 286) (each trade name), each of which is manufactured by Wako Pure Chemical Industries, Ltd.; SR212 (molecular weight 198), SR213 (molecular weight 198), SR349 (molecular weight 468), SR595 (molecular weight 314), SR833 (molecular weight 304), SR351 (molecular weight 296), SR368 (molecular weight 423), SR206 (molecular weight 198), SR214 (molecular weight 226), SR239 (molecular weight 254), and CD262 (molecular weigh 338) (each trade name), each of which is manufactured by SARTOMER Inc.; VISCOAT #195, 1,4-BDDA (molecular weight of 198), VISCOAT #230, HDDA (molecular weight 226), VISCOAT #260, 1,9-NDDA (molecular weight 268), and VISCOAT #335 HP, TEGDA (molecular weight 302) (each trade name), each of which is manufactured by Osaka Organic Chemical Industry Ltd.; and A-DCP (molecular weight 304), A-DOD-N (molecular weight 282), A-HD-N (molecular weight 226), A-NOD-N (molecular weight 268), DCP (molecular weight 332), DOD-N (molecular weight 310), HD-N (molecular weight 254), and NOD-N (molecular weight 298) (each trade name), each of which is manufactured by Shin-Nakamura Chemical Co., Ltd.; and LIGHT ACRYLATE MOD-A (molecular weight 268) and LIGHT ACRYLATE DCP-A (molecular weight 304) (each trade name), each of which is manufactured by Kyoeisha Chemical Co., Ltd.

Among them, a (meth)acrylate having a bicyclo-ring structure is preferred. In particular, dimethylol-tricyclodecane diacrylate or dimethylol-tricyclodecane dimethacrylate is preferred.

By containing the (meth)acrylate oligomer (a) in the sealing resin composition, a good bendability can be obtained at the time of forming a film. Further, by containing the low molecular weight (meth)acrylate (b) in the sealing resin composition, the sealing resin composition has a low viscosity, and a sealing resin obtained by curing is able to obtain a sealing resin composition having a high crosslinking density. The use of a mixed resin composition of these high molecular weight and low molecular weight (meth) acrylates allows a water vapor barrier property to be enhanced.

One element of enhancement of the water vapor barrier property is to uniformly cure a sealing resin composition which contains these high molecular weight and low molecular weight (meth)acrylates. A uniform state can be evaluated by the compatibility test described below.

Further, in order to obtain a good water vapor barrier property, it is preferred to increase a crosslinking density of the sealing resin after cured to a certain level. For this purpose, the total molar number (molar equivalent) of (meth)acryloyl groups of the (meth)acrylate oligomer (a) and the low molecular weight (meth)acrylate (b) in 100 g of the sealing resin composition are preferably 0.05 mol/100-g or more, more preferably 0.20 mol/100-g or more, and still more preferably 0.30 mol/100-g or more. In this regard, from the viewpoints of elastic modulus and flexibility of the sealing resin, the upper limit thereof is preferably 1.10 mol/100-g or less.

Note that, the molar number S (mol/100-g) of (meth) acryloyl groups in 100 g of the sealing resin composition can be calculated by the following equation.

$$S=(na \times xa)/Mn+(nb \times xb)/M$$

In the equation, in the following order, na, xa, and Mn represent the number of (meth)acryloyl groups in one molecule of the (meth)acrylate oligomer (a), a mass (g) of the (meth)acrylate oligomer (a) in 100 g of the sealing resin composition, and the number-average molecular weight of the (meth)acrylate oligomer (a).

Further, in the following order, nb, xb, and M represent the number of (meth)acryloyl groups in one molecule of the low molecular weight (meth)acrylate (b), a mass (g) of the low molecular weight (meth)acrylate (b) in 100 g of the sealing resin composition, and a molecular weight of the low molecular weight (meth)acrylate (b).

At the time of designing the sealing resin composition, the molar number S of (meth)acryloyl groups in 100 g of the sealing resin composition can be adjusted by the above equation.

Further, in the sealing resin composition after blending each of the constituent materials, the molar number S of (meth)acryloyl groups in 100 g of the sealing resin composition can be obtained by IR measurement, $^1$H-NMR measurement, and the like, each of which is commonly practiced.

A combination of the (meth)acrylate oligomer (a) and the low molecular weight (meth)acrylate (b) may be either a combination of methacrylates or a combination of acrylates, or alternatively a combination of a methacrylate and an acrylate. From the viewpoint that a reaction progresses at a comparable polymerization rate, a combination of methacrylates or a combination of acrylates is preferred. In particular, from the viewpoint of higher polymerization rate, a combination of acrylates is preferred.

<Moisture-Reactive Organometallic Compound (c)>

The moisture-reactive organometallic compound (hereinafter, also referred to as an organometallic compound) (c) in the present invention is preferably a complex compound represented by the following formula (1) $M(XR)_n$.

$$M(XR)_n \qquad \text{formula (1)}$$

In the formula (1), M represents a central metal; XR represents a ligand in which X acts as a donner atom; and n represents a valence of M. When n represents 2 or more, XR may be all the same ligand, or may be composed of 2 or more different kinds of ligands. Further, when there is a plurality of XRs, the plurality of XRs may be a multidentate ligand in which each R bonds to one another.

In general, M is preferably Al, Ti, Zr, or Si. In particular, Al is preferred.

An embodiment in which XR is composed of 2 or more different kinds of ligands is more preferred, because a moisture reactive property can be adjusted due to a difference in dissociation constant of each ligand.

As for the donner atom represented by X, a nitrogen atom, an oxygen atom, and a sulfur atom are preferred in general. Among them, an oxygen atom is preferred.

XR may be an anionic ligand in which a donner atom coordinates in the anionic state, or may be a neutral ligand in which a donner atom coordinates in the neutral state. Further, XR may be a multidentate ligand which is a combination of these ligands.

As the XR, specifically, preferred are: a ligand having a coordinating group in which an alcohol, a carboxylic acid, or a thiol is deprotonated; and a ligand having a ketone, ester, or amine coordinating group. Further, a multidentate ligand in which these ligands bond to one another through the respective R's is also preferred. A divalent ligand is more preferred.

Note that, for convenience sake, the complex compound is represented by $M(XR)_n$, using the atomic valence n of M. However, such a complex compound ordinarily exists as a multimeric complex.

It is preferred that the complex material $M(XR)_n$ reacts with water as shown in the following reaction formula (I).

$$M(XR)_n + xH_2O \rightarrow M(OH)_x(XR)_{n-x} + xRXH \qquad \text{reaction formula (I)}$$

The RXH released by reaction with water is preferably a compound which is well miscible with the (meth)acrylate oligomer (a) and the low molecular weight (meth)acrylate (b) (hereinafter, also referred to as a (meth)acrylic resin). In other words, it is preferred that the XR is such a ligand that the dissociated compound RXH is well miscible with a (meth)acrylic resin.

Specific examples of the complex compound include: aluminum ethylate, aluminum isopropylate, aluminum diisopropylate monosecondary-butylate, aluminum secondary-butylate, aluminum ethylacetoacetate diisopropylate (ALCH), aluminum trisethylacetoacetate (ALCHTR), aluminum alkylacetoacetate diisopropylate (AL-M), aluminum bisethylacetoacetate monoacetylacetonate (ALUMI-CHELATE D), aluminum trisacetylacetonate (ALUMI-CHELATE A), aluminum oxide isopropoxide trimer, aluminum oxide octylate trimer, and aluminum oxide stealate trimer, each of which is available (each manufactured by Kawaken Fine Chemicals Co., Ltd.).

The organometallic compound in the present invention is inactivated by reacting with water as described above. Therefore, the sealing resin composition of the present invention is preferably manufactured and handled under arid conditions. Further, it is preferred that constituting materials of the sealing resin composition of the present invention, including additives described below, are used after being subjected to dewatering in advance.

In particular, in the case where all of the ligands to a central metal are an alkoxide, because of a high reaction activity with water molecule, the organometallic compound is inactivated by a reaction with moisture contained in the atmosphere, in the manufacturing process of the sealing resin composition, which results in lowering of drying capacity.

In view of the above, among the organometallic compounds represented by the above-described formula (1), it is more preferable that an organometallic compound represented by the following formula (2) is utilized, in which a ligand having at least one acetylacetonato coordinating group, coordinates to one central metal.

formula (2)

In the formula (2), M represents a central metal; $R^1$ to $R^3$ each represent an alkyl group, an alkenyl group, or an acyl group, each having the carbon atom number of 1 or more. R represents an alkyl group or an alkoxy group, each having the carbon atom number of 1 or more. R' represents a hydrogen atom or an alkyl group having the carbon atom number of 1 or more.

It is preferred that R is an alkoxy group having the carbon atom number of 1 or more.

From the viewpoint of compatibility with the (meth)acrylic resin, the carbon atom number of 2 or more is preferred. Further, from the viewpoint of a water vapor barrier property, the carbon atom number of 20 or less is preferred.

It is preferred that R' is a hydrogen atom.

In the case where any one of $R^1$ to $R^3$, and R is an aryl group, application to a display having a top emission structure is not preferred, because the absorption wavelength of the compound overlaps with a visible light region.

Among the organometallic compounds represented by the above-described formula (2), an organometallic compound is preferred, which has at least one ligand having an acetylacetonato coordinating group and at least one alkoxide ligand.

Further, as for the organometallic compound represented by the above-described formula (2), an organometallic compound is more preferred, in which bimolecular alkoxide ligands and a monomolecular ligand having an acetylacetonato coordinating group coordinate to one central metal M.

The ligand having an acetylacetonato coordinating group is a divalent ligand having a stable keto-enol structure, and therefore the dissociation constant is small and a reaction activity with a water molecule is low.

For this reason, adjustment of the reaction activity with a water molecule can be achieved, by using the organometallic compound having both an alkoxide ligand having a high reaction activity with a water molecule and a ligand having an acetylacetonato coordinating group which has a low reaction activity.

Specific examples of the organometallic compounds include aluminum ethylacetoacetate diisopropylate (ALCH), aluminum alkylacetoacetate diisopropylate (AL-M) (each manufactured by Kawaken Fine Chemicals Co., Ltd.), and the like.

Further, a state is more preferred, where a moisture-reactive organometallic compound (c) and a metal hydroxide which is a reaction product of the moisture-reactive organometallic compound (c) with water coexist alongside in the sealing resin composition of the present invention.

In general, the organic resin readily absorbs water, and almost often contains moisture of several thousand ppm. It is impractical to carry out dehydration of an organic resin containing such a large amount of moisture, by vacuum drying or ustulation so that the moisture content becomes several ppm or less. For this reason, in the case where an organic light-emitting diode element is sealed with an organic resin in which moisture has not been dehydrated, the organic light-emitting diode element becomes deteriorated due to the moisture in the sealant.

In contrast, by preliminarily dehydrating moisture in the sealing resin composition by the moisture-reactive organometallic compound (c), the moisture in the resin is dehydrated, and the moisture content in the sealing resin composition is enabled to be controlled to several ppm or less. For this reason, the life duration is extended, in which the organic light-emitting diode element is sealed with such a dehydrated sealing resin composition.

Further, the moisture-reactive organometallic compound (c) remaining in the sealing resin composition reacts with moisture invading into an organic light-emitting device after sealed, and plays a role in dehydration.

Further, the moisture-reactive organometallic compound (c) contained in the sealing resin enhances hydrophobicity of the substrate surface. As a result, in the case of a sealing resin having a low affinity with an element (device) substrate or a sealing substrate, the moisture-reactive organometallic compound (c) is effective, because the affinity is improved, and it can be lowered invasion of water from an interface between the sealing resin and the substrate.

Further, if a compatibility of the moisture-reactive organometallic compound (c) with the sealing resin composition is good, the moisture-reactive organometallic compound (c) does not cause phase separation or white turbidity in any of the liquid state before cured and the solid state after cured, so that a high water vapor barrier property is obtained by a synergy effect of a water-absorption effect due to the moisture-reactive organometallic compound and a high affinity (adhesive property) to a substrate. On the other hand, by the resin composition in which the phase separation or the white turbidity can be seen before and after cured, the foregoing effects are not obtained, and therefore a sufficient sealing performance is not exerted.

<Polymerization Initiator (d)>

As for the polymerization initiator (d) in the present invention, preferred are a radical photopolymerization initiator, which generates radicals due to decomposition by an electromagnetic energy ray, such as an ultraviolet ray (UV ray), or a heat decomposition radical polymerization initiator, which generates radicals due to decomposition by heat.

In particular, a radical photopolymerization initiator is preferred, because an organic electronic device, such as an organic light-emitting diode element, is less affected by heat, and also a sealing process becomes simplified.

As for the foregoing radical photopolymerization initiator, an ordinarily used one can be used.

Specifically, examples thereof include: IRGACURE series (for example, 651, 754, 184, 2959, 907, 369, 379, 819) and DAROCURE series (for example, TPO, 1173), QUANTACURE PDO, each of which is commercially available from BAFS Japan Co., Ltd.; and ESACURE series (for example, KIP100F, KIP150, 1001M, KB1, KS300, KL200, ONE, HEA, ITX, TZM, TZT, TPO, KT046), each of which is commercially available from DKSH Japan K.K.

In the present invention, it is preferred to use ketone compounds, such as an acetophenone compound and a benzophenone compound.

The amount of the radical photopolymerization initiator is preferably 0.1 mass % or more, and more preferably from 0.5 to 5 mass % by, with respect to the (meth)acrylate resin involved in a reaction.

In the sealing resin composition of the present invention, it is preferred that from 5 to 30 mass % of the (meth)acrylate oligomer (a), from 40 to 90 mass % of the low molecular weight (meth)acrylate (b), and from 5 to 30 mass % of the moisture-reactive organometallic compound (c) are contained at those rates. Note that, those rates are a respective calculated value, provided that a total mass of the (meth) acrylate oligomer (a), the low molecular weight (meth) acrylate (b), the moisture-reactive organometallic compound (c), and the polymerization initiator (d) is 100 mass %.

If the rate of the (meth)acrylate oligomer (a) is 5 mass % or more, it is excellent in flexibility, and the rate is more preferably 10 mass % or more, and still more preferably 15 mass % or more. Further, if the rate thereof is 30 mass % or less, it is excellent in a water vapor barrier property, and the rate is more preferably 25 mass % or less, and still more preferably 20 mass % or less.

If the rate of the low molecular weight (meth)acrylate (b) is 40 mass % or more, it is excellent in water vapor barrier property, and the rate is more preferably 50 mass % or more, and still more preferably 60 mass % or more. Further, if the rate thereof is 90 mass % or less, it is excellent in flexibility, and the rate is more preferably 85 mass % or less, and still more preferably 80 mass % or less.

If the rate of the moisture-reactive organometallic compound (c) is 5 mass % or more, it is excellent in moisture-removing ability in the sealing resin, and the rate is more preferably 10 mass % or more, and still more preferably 15 mass % or more. Further, if the rate thereof is 30 mass % or less, it is excellent in a water vapor barrier property, and the rate is more preferably 25 mass % or less, and still more preferably 20 mass % or less.

(Additives)

The sealing resin composition of the present invention may contain any of other additives, to the extent in which they do not deteriorate the water vapor barrier property or bendability of the sealing resin. Examples of the foregoing additives include: a diluent, a tackifier, a crosslinking aid, a frame retardant, a polymerization inhibitor, a filler, a coupling agent, and the like.

Examples of the diluent include: a low-viscosity (meth) acrylic monomer or polybutene. Examples of the tackifier include: a rosin-based resin, a petroleum-based resin, a terpene-based resin, a chromane resin, hydrated compounds of these resins, or the like.

Further, in order to enhance the attachment thereof to a sealing object, the sealing resin composition of the present invention may contain an epoxy group-containing resin and a cationic polymerization initiator, and resins whose polymerization is initiated by a cationic polymerization initiator.

The compatibility test in the pre-cured state after blending of the sealing resin composition, can be conducted in accordance with the following method.

Firstly, the (meth)acrylate oligomer (a), the low molecular weight (meth)acrylate (b), the moisture-reactive organometallic compound (c), and the polymerization initiator (d) are blended so that a total amount thereof would be 10 g, at a blend ratio of the components which constitutes the sealing resin composition, and then the mixture is stirred at ordinary temperature (23° C.) for 1 hour. The sealing resin composition after stirring is left to stand. Then, the states after 1 hour and after 24 hours are confirmed with the naked eye.

Regarding the sealing resin composition, a uniform state is preferred, and a uniformly transparent state without white turbidity is more preferred.

Note that, a two layer-separated state is not preferred, because it is impossible to uniformly cure the composition.

Further, the compatibility test in the state after cured the blended sealing resin composition can be conducted in accordance with the following method. Note that, the sealing resin composition after still stood for 24 hours, which was used in the above-described compatibility test, is used as a sealing resin composition in this test.

Firstly, the sealing resin composition is coated on a 50 μm-thick releasing-processed polyethylene terephthalate film (PET film) (trade name "E7004", manufactured by Toyobo Co., Ltd.) at the thickness of 100 μm, and further a 25 μm-thick releasing-processed PET film (trade name "E7004", manufactured by Toyobo Co., Ltd.) is laminated on the coated sealing resin composition. Then, 3 J/cm$^2$ of ultraviolet ray is irradiated using an ultraviolet irradiator to the sealing resin composition, which has been sandwiched with 2 sheets of the releasing-processed PET films, and then the sheets of the releasing-processed PET films are separated. Thus, a cured film of the sealing resin composition was obtained. The state of the cured film is confirmed with the naked eye.

Regarding the cured film, a uniformly transparent state is preferred, and a clouded state is not preferred, because it indicates that a uniform curing has not been achieved.

Measurement of the resin viscosity can be conducted in accordance with the following method.

The above-prepared pre-cured sealing resin composition is left to stand for 1 hour, and then a complex viscosity n* at an ordinary temperature (25° C.) at an angular velocity of shear rate of 1 s$^{-1}$ is measured in a dynamic viscoelasticity measuring instrument (instrument name "ARES", manufactured by Leometric Scientific F. E. Co., Ltd.) using a cone plate having a cone diameter of 25 mm and a cone angle of 0.1 rad.

The complex viscosity n* of the sealing resin composition is preferably 5 Pa·s or less, and more preferably 2 Pa·s or less. If the complex viscosity n* is as high as more than 5 Pa·s, coating work to a sealing substrate becomes difficult.

Specifically, the complex viscosity n* is preferably 2 Pa·s or less in particular, and the range of more than 2 Pa·s and 5 Pa·s or less is secondly preferred.

The bendability test can be conducted in accordance with the following method.

The 100 μm-thick cured film of the sealing resin composition is used as a test object, which is prepared at the above-described compatibility test of the sealing resin composition after cured. The test of this test object is conducted using a mandrel having a diameter of 2 mm and a mandrel having a diameter of 4 mm, according to the bending resistance described in JIS K 5600-5-1 (cylindrical mandrel method).

As to the cured film, it is preferred that with respect to the mandrel having a diameter of 4 mm, none of whitening and breaking is caused and also there is no cracking, and further it is more preferred that with respect to the mandrel having a diameter of 2 mm, none of whitening and breaking is also caused and also there is no cracking.

Note that, the smaller the diameter of the mandrel becomes, the higher the required bendability becomes.

By a fact that the bendability is within the above-described preferable range, even when a resin film having bendability or an ultrathin glass film is used for a substrate, a sealing resin bends moving on with the substrate and does not break away.

The water vapor barrier property test can be conducted in accordance with the following method.

A 100 μm-thick cured film of a sealing resin composition is used as a test object, which is prepared in the same manner as the compatibility test in the state after cured the above-described curable and hygroscopic resin composition for sealing electronic devices, from which the moisture reactive organometallic compound (c) is removed. The moisture permeability is measured under the conditions of 40° C. and 90% relative humidity, with reference to the moisture permeability test method (cup method) of the moisture-proof packaging material described in JIS Z 0208.

Note that, when a sample film was put into a thermostat of 40° C. and 90% relative humidity, there is a danger that the film swells due to a change in volume of the air in the cup, so that the surface area and the thickness of the sample film are changed, and as a result, the measured value becomes inaccurate. For this reason, the sample is reinforced with a 20 μm-thick cellophane tape. The moisture permeability of the 20 μm-thick cellophane tape is 3,000 g/m$^2$/24-hr at the same condition as the above, which is much larger than the moisture permeability of the sample to be measured in the present invention, and therefore the cellophane tape does not interfere with the measurement in the moisture permeability of the sample.

The moisture permeability of a 100 μm-thick cured film to be measured in the above-described water vapor barrier property test, which is formed by curing the above-described curable and hygroscopic resin composition for sealing electronic devices from which a moisture-reactive organometallic compound (c) is removed, is preferably 10 g/m$^2$/24-hr or less, and more preferably 7 g/m$^2$/24-hr or less, under the conditions of 40° C. and 90% relative humidity. Note that, the lower limit thereof is 1 g/m$^2$/24-hr or more in practice.

By adding the moisture-reactive organometallic compound (c) to the composition having the above-described preferable range of the water vapor barrier property (moisture permeability), a sealing resin is able to sufficiently exert an effect on the water vapor barrier.

Further, using the same test object as the above-described bendability test as a sample, the moisture permeability of a 100 μm-thick cured film to be measured by the above-described water vapor barrier property test, which is formed by curing the sealing resin composition of the present invention, is preferably 30 g/m$^2$/24-hr or less, and more preferably 20 g/m$^2$/24-hr or less, under the conditions of 40° C. and 90% relative humidity. Note that, the lower limit thereof is 10 g/m$^2$/24-hr or more in practice.

The Ca corrosion test can be conducted in accordance with the following method.

A commercially-available glass substrate having dimensions of 1.2 mm×22.5 mm×14 mm is subjected to an ultrasonic cleaning and an UV-ozone cleaning at 45° C. for 10 minutes. Then, on the glass substrate, a metal calcium layer having dimensions of 10 mm×10 mm square and thickness of 100 nm is formed by vacuum deposition equipment. Then, 10 μL of a liquid sealing resin composition is put drop-wise on the metal calcium layer, so that the thickness of the sealing resin after cured would be 30 μm, and further a sealing glass of 0.15 mm×18 mm×18 mm is put on a top of the metal calcium layer, and then 3 J/cm$^2$ of ultraviolet ray is irradiated using an ultraviolet irradiator, to seal the metal calcium layer, thereby obtaining a test specimen.

Figures 5A, 5B:
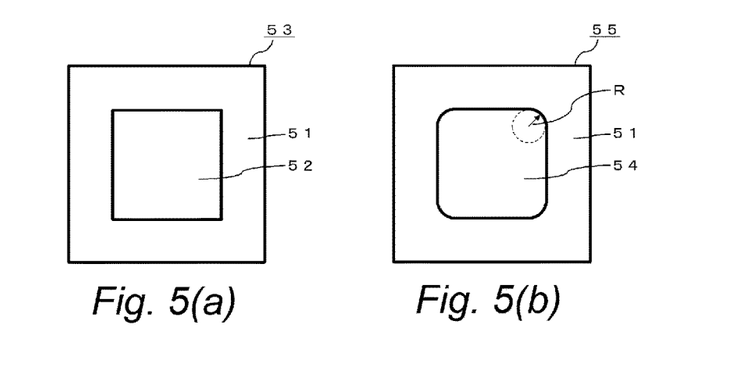
FIG. 5(a) is an overhead view showing a test specimen to be used for a Ca corrosion test and FIG. 5(b) is an overhead view showing a corroded state of four corners of the test specimen used for a Ca corrosion test, in Examples and Comparative Examples.

Herein, a distance from an outer circumferential side of the sealing glass to an outer circumferential side of the metal calcium layer is equally set to 4 mm in each of 4 sides. FIG. 5(a) is an overhead view (however, the above-described sealing glass is omitted) of the above-described test specimen which can be seen through a glass substrate (using a transparent glass).

The obtained test specimen is stored under high-temperature and high-humidity of 60° C. and 90% relative humidity, and then a corner portion of the metal calcium 54 after a lapse of 48 hours is observed.

Note that, this Ca corrosion test is to measure a sealing capability of the sealing resin, by using a fact that silver-white-colored metal calcium having a metallic luster, which has been sealed with the resin on a glass substrate, reacts with a water molecule invading into the resin to form a transparent calcium hydroxide. For this reason, this test is a test method which is closer to an image of the actual sealing.

More specifically, with a progress of corrosion, the eroded portion becomes a transparent calcium hydroxide. For this reason, the corner portion of the silver-white-colored metal calcium 54 having a metallic luster is seen roundly. The corrosion degree in this test can be evaluated, by using a curvature radius R at the corner portion of the metal calcium 54, as shown in FIG. 5(b).

The curvature radius R of the roundness of calcium due to corrosion is preferably a range of 1 mm or more and less than 5 mm, and more preferably a range of more than 0 mm and less than 1 mm. The corner whose R is 0 mm, in other words, without corrosion, is still more preferred.

Herein, the sealing resin, which shows low moisture permeability in the above-described water vapor barrier property test, often obtains a good appraisal also in this Ca corrosion test.

However, the entry rout of the water molecule includes: a rout through the sealing resin from a contact face between the atmosphere and the sealing resin; and in addition a rout through an interface (sealing interface) between the sealing resin and a substrate. For this reason, if affinity between the sealing resin and the substrate is not enough, an affection of moisture routed through the sealing interface becomes larger, so that appraisals of the water vapor barrier property test and the Ca corrosion test sometimes discord from each other.

Among the above-described evaluation tests, the appraisal in the Ca corrosion test is most important as an indicator of the water vapor barrier property with respect to the sealing resin. Then, the appraisal of the resin viscosity involved in sealing workability is important, and in turn, the appraisal in the bendability test is important <<Sealing Resin>>

The sealing resin of the present invention can be obtained, by forming the above-described resin composition of the present invention in the form of a film, and then curing the same. A specific effect which can be achieved by using the sealing resin of the present invention for an electronic device and the like, is described in the following section of the electronic device.

<<Electronic Device>>

The electronic device of the present invention is an electronic device, especially an organic electronic device, sealed by using the above-described resin composition of the present invention.

Hereinafter, as an example of the organic electronic device, an organic light-emitting device (image display device) is described.

An organic light-emitting device 5 is a so-called top emission or bottom emission light-emitting device. As shown in FIG. 1, an organic light-emitting diode element 3 provided on an element substrate 4 is sealed with a sealing substrate 1 through a sealing resin 2. Note that, the sealing resin 2 means a resin which is formed by curing the sealing resin composition of the present invention.

Note that, as to the foregoing organic light-emitting device 5, a sealing lateral face thereof may be exposed. In other words, an additional sealing processing is not necessarily conducted, by a glass frit, an adhesive, or the like, as a sidewall sealant. This is attributed to a fact that the sealing resin composition of the present invention has both high water vapor barrier property and adhesion property. As just described, because such an additional sealing processing is not necessarily conducted, by a glass frit, or the like. Thus, the resultant structure of the organic light-emitting device 5 can be simplified, and a weight saving and a cost saving can be achieved.

Further, because a rigid glass frit or the like is not used, in the case where a flexible material is used for an element substrate 4 or a sealing substrate 1, the provision of a so-called flexible device becomes possible, in which flexibility has been given to the organic light-emitting device 5 itself. Further, the device as a whole is flexible and light-weight, and therefore becomes hard to destructible, even if the device is subjected to impact, such as a fall.

Figure 2:
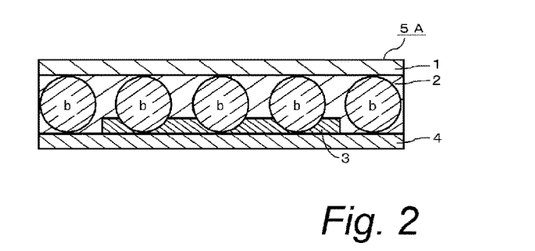
FIG. 2 is a schematic cross-sectional view showing one embodiment in which an organic light-emitting diode element is sealed with the curable and hygroscopic resin composition for sealing electronic devices of the present invention, together with a spacer for a uniform sealing.

In the present invention, other than the organic light-emitting device 5 as shown in FIG. 1, an organic light-emitting device 5A as shown in FIG. 2 is also preferred. In FIG. 2, in order to place a sealing substrate 1 and an element substrate 4 parallel to one another, a spacer b having a proper height to the intended thickness of the sealing resin is incorporated into the device.

Unless the height of the spacer b to be used is practically the same in any spacer b, it becomes difficult to place the sealing substrate 1 and the element substrate 4 parallel to one another.

As to the spacer b, it is preferred to use a spherical shaped filler, or a pillared pillar formed by a photolithography. Further, as to the material thereof, either organic or inorganic materials may be adopted, unless there is a danger that any of them crushes and destroys an organic light-emitting diode element with a pressure at the time of sealing. Note that, as regards the material, an organic resin is preferred, because the organic resin is excellent in affinity to the sealing resin composition of the present invention, and a cross-linked acrylic resin is more preferred, because deterioration of the gas barrier property is lessened.

Examples of the spacer b include: ENEOS Uni-Powder manufactured by JX Nippon Oil & Energy Corporation, HAYABEADS manufactured by Hayakawa Rubber Co., Ltd., and the like.

The placement density of the spacer b per $mm^2$ of the substrate is preferably $10/mm^2$ or more, more preferably $50/mm^2$ or more, and still more preferably $100/mm^2$ or more, form the viewpoint of placing the sealing substrate 1 and the element substrate 4 parallel to one another. If the placement density is less than $10/mm^2$, it becomes difficult to uniformly maintain a distance between the upper substrate and the lower substrate.

From the viewpoint of a resin viscosity, the placement density of the spacer per $mm^2$ of the substrate is preferably $1,000/mm^2$ or less, more preferably $500/mm^2$ or less, and still more preferably $300/mm^2$ or less. If the placement density is more than $1,000/mm^2$, the resin viscosity becomes too high, and resultantly the sealing working becomes difficult.

From the viewpoint of a surface asperity-tracking performance with respect to a substrate (sealing face), the thickness of the sealing resin is preferably 0.5 μm or more, more preferably 1 μm or more, and still more preferably 2 μm or more. If the thickness of the sealing resin is less than 0.5 μm, irregularity of the organic light-emitting diode element cannot be sufficiently absorbed, and resultantly a space between substrates cannot be completely sealed.

Further, from the viewpoint of a water vapor barrier property, the thickness of the sealing resin is preferably 100 μm or less, more preferably 50 μm or less, and still more preferably 30 μm or less. If the thickness of the sealing resin is more than 100 μm, the area of the sealing resin exposing to the atmosphere increases, so that a sealing effect lowers, because a moisture intrusion amount becomes larger.

Note that, when a spacer b is used, the thickness of the sealing resin corresponds to a height of the spacer b.

Figure 3:
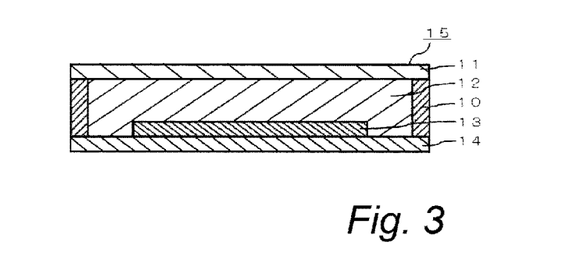
FIG. 3 is a schematic cross-sectional view showing another embodiment in which an organic light-emitting diode element is sealed with the curable and hygroscopic resin composition for sealing electronic devices of the present invention.

The sealing resin composition of the present invention may be used for the organic light-emitting device 15, which is subjected to an additional hermetic sealing with a sidewall sealant (a glass frit or an adhesive) 10 or the like, as shown in FIG. 3. In this case, a high airtightness is maintained, due to a synergetic effect between the sealing resin composition of the present invention and the sidewall sealant (the glass frit or the adhesive) 10. For this reason, an organic light-emitting device 15, in which a sealing resin 12 obtained from the sealing resin composition of the present invention is used in combination with the sidewall sealant (the glass frit or the adhesive) 10, is preferred, from the viewpoint of realizing a long life of the organic light-emitting device 15.

A production method of the organic light-emitting device using the sealing resin composition of the present invention is as follows.

Regarding the organic light-emitting device 5 which has not been subjected to a hermetic sealing at a frame portion as shown in FIG. 1, firstly, on an organic light-emitting diode element substrate 4 on which organic EL element parts have been formed in the form of lamination, a suitable amount of the sealing resin composition of the present invention is coated so as to cover an organic light-emitting diode element 3, and further a sealing substrate 1 is placed thereon from above so as to sandwich the sealing resin composition of the present invention in between the element substrate 4 and the sealing substrate 1. In this way, a hermetic sealing is performed so as not to form voids in between the element substrate 4 and the sealing substrate 1. After that, the sealing resin composition of the present invention is cured by ultraviolet irradiation, to form a sealing resin 2, so that a sealing is completed.

Alternatively, at the beginning, a sealing resin composition of the present invention is coated on a sealing substrate 1, and then an organic light-emitting diode element 3 is placed on the sealing resin composition, and after sandwiching them in between the sealing substrate and an element substrate 4, the sealing resin composition of the present invention is cured by ultraviolet irradiation, to form a sealing resin 2. Thus, the sealing is also completed.

In the case of a structure as shown in FIG. 3, whose dam structure portion is formed surrounding around an organic light-emitting diode element 13 with an adhesive, a gas-barrier sealant, or a glass frit-hardened material, as a side-wall sealant 10, thereby lowering moisture invasion from a sealing edge, at the beginning, the sidewall sealant (adhesive) 10 is formed on an element substrate 14 or a sealing substrate 11. After that, a sealing resin composition of the present invention is poured into the inside of the sidewall sealant (adhesive) 10 formed around the forgoing organic light-emitting diode element 13, and further another substrate is placed so as to sandwich the sealing resin composition of the present invention in between the one substrate and the another substrate. In this way, a hermetic sealing is performed so as not to form voids in between the element substrate 4 and the sealing substrate 1. After that, the sealing resin composition of the present invention is cured by ultraviolet irradiation, to form a sealing resin 2 thereby completing a sealing.

If these sealing processes are carried out under the drying environment, deterioration in the hygroscopic nature of the sealing resin composition of the present invention is preferably lessened.

Figure 4:
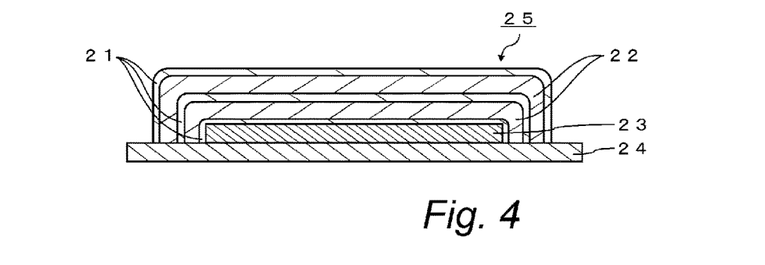
FIG. 4 is a schematic cross-sectional view showing still another embodiment in which an organic light-emitting diode element is sealed with the curable and hygroscopic resin composition for sealing electronic devices of the present invention.

Further, the sealing resin obtained from the sealing resin composition of the present invention may be used for an organic light-emitting device 25 as shown in FIG. 4, which is formed by the following steps of coating a sealing resin composition of the present invention on an inorganic thin film 21 covering an entire upper side of an organic light-emitting diode element 23 formed on a gas-barrier element substrate 24, and then curing the sealing resin composition, to provide an organic thin film 22, and further forming thereon an inorganic thin film 21, to obtain a plurality of laminates composed of the organic thin film 22 and the inorganic thin film 21, whereby a hermetic sealing is completed. In this case, the organic resin acts as the sealing resin. A high airtightness is maintained, due to a synergetic effect between the organic thin film 22 obtained from the sealing resin composition of the present invention and the inorganic thin film 21. The number of laminates is not limited to the embodiment shown in FIG. 4, but is arbitrarily designed, as long as the above-described effect can be obtained.

Herein, the inorganic thin film 21 is composed of a silicon nitride compound, a silicon oxide compound, an aluminum oxide compound, aluminum, or the like. Formation of the inorganic thin film 21 is carried out by plasma CVD (PECVD), PVD (physical vapor deposition), ALD (atomic layer deposition), or the like. The thickness of one layer of the inorganic thin film 21 is preferably 1 μm or less, from the viewpoint of bendability.

The organic thin film 22 is formed by coating a resin composition using an existing method, such as an ink jetting method, a spray coating method, a slit coating method, and a bar coating method, and then curing the resin composition by ultraviolet irradiation. The thickness of one layer of the organic thin film 22 is preferably 5 μm or less, from the viewpoint of bendability, but preferably 1 μm or more, and more preferably 5 μm or more, from the viewpoint of impact resistance to an organic EL element.

In the organic light-emitting device using the sealing resin composition of the present invention, a color filter for chromaticity adjustment may be installed. Regarding an installation location of the color filter in this case, in the case of the embodiments shown in FIGS. 1 to 3, the color filter may be installed in between the sealing resin 2(12) and the sealing substrate 1(11) or the element substrate 4(14), or the color filter may be installed so as to sandwich the element substrate 4(14) in between the color filter and an organic light-emitting diode element 3(13), or alternatively may be installed so as to sandwich the sealing substrate 1(11) and the sealing resin 2(12) in between the color filter and the element substrate 4(14). In the case of the embodiment shown in FIG. 4, the color filter may be installed on the top of the inorganic thin film 21, or below the element substrate 24. In this case, it is preferred that the color filter is immobilized with the sealing resin composition of the present invention or another transparent resin composition.

EXAMPLES

The present invention will be described in more detail based on examples given below, but the invention is not meant to be limited by these.
(Meth)acrylate oligomer (a)
Preparation of acrylate oligomer (a-1)
As a basic resin (aa), 20 g of a liquid polybutadiene having a hydroxyl group GI-1000 (the number-average molecular weight 1,500, manufactured by Nippon Soda Co., Ltd.) was poured into a nitrogen-substituted flask. To the liquid polybutadiene GI-1000 under agitation, 3.8 g of 2-isocyanatoethyl acrylate (trade name "KARENZ AOI", manufactured by Showa Denko K.K.), as a compound (ab) having a functional group and an acryloyl group, was added drop-wise spending 10 minutes. By allowing the resultant mixture as it is to react for 2 hours, to prepare the acrylate oligomer (a-1) (the number-average molecular weight 1,800, the number of acryloyl groups in one molecule 2.0).
Preparation of acrylate oligomers (a-2) to (a-6), (a-13), and (a-14)

Acrylate oligomers (a-2) to (a-5), (a-13), and (a-14) were prepared in the same manner as the acrylate oligomer (a-1), except that the respective basic resin (aa) in the composition shown in Table 1 was used in place of the GI-1000 in the acrylate oligomer (a-1), and that the blended mass ratio was changed so as to be the number of acryloyl groups shown in Table 1.

Further, methacrylate (a-6) was prepared in the same manner as the acrylate oligomer (a-1), except that 2-isocyanatoethyl methacrylate (trade name "KARENZ MOI", manufactured by Showa Denko K.K.) as a compound (ab) having a functional group and an acryloyl group was used in place of 2-isocyanatoethyl acrylate in the acrylate oligomer (a-1), and that the blended mass ratio was changed so that the number of methacryloyl groups in one molecule was 2.0.

Regarding (meth)acrylate oligomers (a-7) to (a-12), and (a-15), commercially available products shown in Table 1 were used without any change.

(Meth)acrylate oligomers (a-1) to (a-15) are shown together in the following Table 1.

Herein, the number-average molecular weight is calculated by subjecting a 1% solution of the (meth)acrylate oligomer dissolved in tetrahydrofuran (solvent name) to gel permission chromatography (GPC system, manufactured by Waters Corporation, column: "TSKgel GMHHR-N", manufactured by Tosoh Corp., flow rate: 1.0 mL/min), and converting the measured value into the polystyrene conversion number-average molecular weight.

Further, the number of (meth)acryloyl groups in one molecule is a value calculated by $^1$H-NMR measurement. In Table 1, the number of (meth)acryloyl groups in one molecule was abbreviated as the number of (meth)acryloyl moieties.

TABLE 1

| | Composition | Blended mass (g) | | The number average molecular weight | The number of (meth)acryloyl groups |
|---|---|---|---|---|---|
| | | Basic resin (aa) | AOI or MOI (ab) | | |
| a-1 | GI-1000 (modified by AOI) | 20 | 3.8 | 1,800 | 2.0 |
| a-2 | GI-2000 (modified by AOI) | 20 | 2.7 | 2,400 | 2.0 |
| a-3 | GI-3000 (modified by AOI) | 20 | 1.9 | 3,300 | 2.0 |
| a-4 | HLBH-P 2000 (modified by AOI) | 20 | 2.7 | 2,400 | 1.9 |
| a-5 | HLBH-P 3000 (modified by AOI) | 20 | 1.9 | 3,400 | 1.9 |
| a-6 | GI-1000 (modified by MOI) | 20 | 4.4 | 1,800 | 2.0 |
| a-7 | CN307 | — | — | 3,500 | 2.0 |
| a-8 | CN308 | — | — | 3,800 | 2.0 |
| a-9 | CN9014 | — | — | 4,300 | 2.0 |
| a-10 | TE-2000 | — | — | 2,500 | 2.0 |
| a-11 | TEAI-1000 | — | — | 2,000 | 2.0 |
| a-12 | EMA-3000 | — | — | 3,100 | 2.0 |
| a-13 | Poly bdR-20LM Resin (modified by AOI) | 20 | 4.2 | 1,400 | 2.5 |

TABLE 1-continued

| Composition | Blended mass (g) | | The number average molecular weight | The number of (meth)acryloyl groups |
|---|---|---|---|---|
| | Basic resin (aa) | AOI or MOI (ab) | | |
| a-14 LBH 10000 (modified by AOI) | 20 | 0.6 | 10,000 | 1.9 |
| a-15 BRENMER DA-800AU | — | — | 800 | 2.0 |

Note that, the materials used in the (meth)acrylate oligomer (a) are shown below.
Basic Resin (aa)
GI-1000 (a hydrogenated polybutadiene having hydroxyl groups at its both ends, manufactured by Nippon Soda Co., Ltd., the number-average molecular weight 1,500)
GI-2000 (a hydrogenated polybutadiene having hydroxyl groups at its both ends, manufactured by Nippon Soda Co., Ltd., the number-average molecular weight 2,100)
GI-3000 (a hydrogenated polybutadiene having hydroxyl groups at its both ends, manufactured by Nippon Soda Co., Ltd., the number-average molecular weight 3,000)
KRASOL HLBH-P2000 (a hydrogenated polyolefin having a hydroxyl group at its end, manufactured by Cray Valley, the number-average molecular weight 2,100)
KRASOL HLBH-P3000 (a hydrogenated polyolefin having a hydroxyl group at its end, manufactured by Cray Valley, the number-average molecular weight 3,100)
Poly bdR-20LM Resin (a hydrogenated polyolefin having a hydroxyl group at its end, manufactured by Cray Valley, the number-average molecular weight 1,200)
KRASOL HLBH 10000 (a hydrogenated polyolefin having a hydroxyl group at its end, manufactured by Cray Valley, the number-average molecular weight 10,000)
Compound (ab) Having a Functional Group and an Acryloyl Group
KARENZ AOI (a 2-isocyanatoethyl acrylate, manufactured by Showa Denko K.K.)
KARENZ MOI (a 2-isocyanatoethyl methacrylate, manufactured by Showa Denko K.K.)
(Meth)acrylate oligomer (a)
CN307 (a hydrophobic acrylate oligomer, manufactured by SARTOMER Inc.)
CN308 (a hydrophobic acrylate oligomer, manufactured by SARTOMER Inc.)
CN310 (a hydrophobic aliphatic urethane acrylate, manufactured by SARTOMER Inc.)
CN9014 (a hydrophobic aliphatic urethane acrylate, manufactured by SARTOMER Inc.)
TE-2000 (a uretrhane dimethacrylate resin having a polybutadiene at its end, manufactured by Nippon Soda, Co., Ltd.)
TEAM 000 (a uretrhane diacrylate resin having a polybutadiene at its end, manufactured by Nippon Soda, Co., Ltd.)
EMA-3000 (a methacrylate resin having a polybutadiene at its end, manufactured by Nippon Soda, Co., Ltd.)
BRENMER DA-800AU (a polyethyleneglycol diacrylate resin, manufactured by NOF Corporation)
Preparation of a Curable and Hygroscopic Resin Composition for Sealing Electronic Eevices Example 1

To a container, added were 7 g of CN9014 (manufactured by SARTOMER Inc.) as the acrylate oligomer (a-9), 89 g of ethylene diacrylate (manufactured by Wako Pure Chemical Industries, Ltd.) as the low molecular weight acrylate (b), 3 g of aluminum trisethylacetoacetate (trade name "AICH-TR", manufactured by Kawaken Fine Chemicals Co., Ltd.) as the moisture-reactive organometallic compound (c), and 1 g of ESACURE TZT (trade name, manufactured by DKSH Japane Co., Ltd.) as the polymerization initiator (d), followed by siring until the resultant mixture would become uniform, to obtain a sealing resin composition.

Examples 2 to 29 and Comparative Examples 1 to 9

Sealing resin compositions of Examples 2 to 29 and Comparative Examples 1 to 9 were prepared in the same manner as in Example 1, except that the constituting materials shown in Tables 2 to 4 were used in the masses shown in Tables 2 to 4, respectively, in place of the constituting materials used in Example 1.

Note that, the mass unit (g) of the constituting materials (a) to (d) in Tables 2 to 4 was omited from the description.
<The Mole Number of (Meth)Acryloyl Groups>

With respect to the sealing resin compositions of Examples 1 to 29 and Comparative Examples 1 to 9 prepared above, the mole number S (mol/100-g) of (meth)acryloyl groups in 100 g of the sealing resin composition was calculated by the following formula.

$$S=(na \times xa)/Mn+(nb \times xb)/M$$

In the equation, in the following order, na, xa, and Mn represent the number of (meth)acryloyl groups in one molecule of the (meth)acrylate oligomer (a), a mass (g) of the (meth)acrylate oligomer (a) in 100 g of the sealing resin composition, and the number-average molecular weight of the (meth)acrylate oligomer (a).

Further, in the following order, nb, xb, and M represent the number of (meth)acryloyl groups in one molecule of the low molecular weight (meth)acrylate (b), a mass (g) of the low molecular weight (meth)acrylate (b) in 100 g of the sealing resin composition, and a molecular weight of the low molecular weight (meth)acrylate (b).

Herein, the mole number of acryloyl groups in 100 g of the sealing resin composition with respect to the sealing resin composition of Example 25 was calculated by $^1$H-NMR measurement, and the obtained value was 0.44 mol/100-g. The mole number of acryloyl groups in the sealing resin composition of Example 25 calculated from the above formula was 0.40 mol/100-g, so that a nearly equal value was obtained by any of the methods of the calculation formula and the measurement, whichever method was used.

Note that, in Tables 2 to 4, the mole number of (meth)acryloyl groups in 100 g of the sealing resin composition was described as the mole number (mol/100-g) of (meth)acryloyl groups.

With respect to the sealing resin compositions of Examples 1 to 29 and Comparative Examples 1 to 9 prepared above, the following evaluations were conducted.

<Compatibility Test (After Blended but Before Cured)>

The blended ratio shown in Tables 2 to 4 of the (meth) acrylate oligomer (a), the low molecular weight (meth) acrylate (b), the moisture-reactive organometallic compound (c), and the polymerization initiator (d) were blended so as to be a total of 10 g in the blend ratio shown in Tables 2 to 4, followed by stirring at room temperature for 1 hour. After stirring, the sealing resin compositions was left to stand. The state after 1 hour and the state after 24 hours were confirmed with the naked eye.

A uniformly transparent state was rated as "A" (good), a uniformly cloudy state was rated as "C" (passed), and a two-layer separated state was rated as "D" (poor).

Note that, in Tables 2 to 4, evaluation of the compatibility test was described as Compatibility test (1 hour after blended but before cured) and Compatibility test (24 hours after blended but before cured).

<Compatibility Test (After Cured)>

The above-described sealing resin composition after still standing for 24 hours was coated so as to have the thickness of 100 μm on a 50 μm-thick release-processed PET film (trade name "E7004", manufactured by Toyobo Co., Ltd.), and further a 25 μm-thick release-processed PET film (trade name "E7004", manufactured by Toyobo Co., Ltd.) was laminated on the coated sealing resin composition. To the sealing resin composition sandwiched with 2 sheets of the release-processed PET films, 3 J/cm² of ultraviolet ray was irradiated using an ultraviolet irradiator, and then the 2 sheets of release-processed PET films were stripped off, to obtain a cured film of the sealing resin composition. The state of the cured film was confirmed with the naked eye.

A uniformly transparent state was rated as "A" (good), and a cloudy state was rated as "D" (poor).

<Viscosity Measurement>

The sealing resin composition prepared in the above-described compatibility test (after blended but before cured) was left to stand for 1 hour, and then a complex viscosity n* at an angular velocity of shear rate of 1 s⁻¹ and an ordinary temperature (25° C.) was measured, in a dynamic viscoelasticity measuring instrument (instrument name "ARES", manufactured by Leometric Scientific F. E. Co., Ltd), using a cone plate having a cone diameter of 25 mm and a cone angle of 0.1 rad.

The resin composition having the complex viscosity n* of 2 Pa·s or less was rated as "AA" (excellent). The resin composition having the complex viscosity n* of more than 2 Pa·s and 5 Pa·s or less was rated as "A" (good). The resin composition having the complex viscosity n* of more than 5 Pa·s was rated as "D" (poor).

<Bendability Test>

The 100 μm-thick cured film of the sealing resin composition, which was prepared at the above-described compatibility test of the sealing resin composition (after cured), was used as a test object. The test of this test object was conducted, using a mandrel having a diameter of 2 mm and a mandrel having a diameter of 4 mm, with reference to the flex resistance described in JIS K 5600-5-1 (cylindrical mandrel method).

The cured film in which none of whitening, breaking, and cracking was observed, was judged as accepted in the test, and that cured film which was judged as accepted in the test, under both the mandrel having a diameter of 2 mm and the mandrel having a diameter of 4 mm, was rated as "AA" (excellent). The cured film, which was judged as accepted in the test, under only the mandrel having a diameter of 4 mm, was rated as "A" (good). The cured film, which was not judged as failed in the test (not passed the test), under both the mandrel having a diameter of 2 mm and the mandrel having a diameter of 4 mm, was rated as "D" (poor).

<Water Vapor Barrier Test>

A 100 μm-thick cured film of the sealing resin composition, which was prepared in the same manner as the above-described compatibility test (after cured), except that the moisture-reactive organometallic compound (c) was removed therefrom, was used as a test object. The moisture permeability was measured, under the condition of 40° C. and 90% relative humidity, with reference to the moisture permeability test method (cup method) of the moisture-proof packaging material described in JIS Z 0208.

Note that, when a film is put into a thermostat of 40° C. and 90% relative humidity, there is a danger that the film swells due to a change in volume of the air in the cup, so that the surface area and the thickness of the sample film are changed, and as the result, the measured value becomes inaccurate. For this reason, the sample was reinforced with a 20 μm-thick cellophane tape. The moisture permeability of the 20 μm-thick cellophane tape is 3,000 g/m²/24-hr at the same condition as the above, which is much larger than the moisture permeability of the sample of each of Examples and Comparative Examples, and therefore the cellophane tape does not interfere with the measurement in the moisture permeability of the sample.

<Ca Corrosion Test>

The Ca corrosion test is described appropriately with reference to FIG. 5.

A commercially-available glass substrate (transparent glass) having dimensions of 1.2 mm×22.5 mm×14 mm was subjected to an ultrasonic cleaning and an UV-ozone cleaning at 45° C. for 10 minutes. Then, on the glass substrate, a metal calcium layer having dimensions of 10 mm×10 mm square and thickness of 100 nm was formed by vacuum deposition equipment. Then, 10 μL of a liquid sealing resin composition was put drop-wise on the metal calcium layer so that the thickness of the sealing resin after cured would be 30 μm, and further a sealing glass (transparent glass) of 0.15 mm×18 mm×18 mm was put on a top of the metal calcium layer, and then 3 J/cm² of ultraviolet ray was irradiated using an ultraviolet irradiator, to seal the metal calcium layer, thereby obtaining a test specimen.

Herein, a distance from an outer circumferential side of the sealing glass to an outer circumferential side of the metal calcium layer, was equally set to 4 mm in each of 4 sides. FIG. 5(a) is an overhead view (however, the above-described sealing glass portion is omitted) of the above-described test specimen which can be seen through a glass substrate.

The obtained test specimen was stored under high-temperature and high-humidity of 60° C. and 90% relative humidity, and then a corner portion of the metal calcium 54 after a lapse of 48 hours was observed.

Note that, this Ca corrosion test is to measure a sealing capability of the sealing resin, by using a fact that silver-white-colored metal calcium having a metallic luster which has been sealed with a resin on the glass substrate, reacts with water molecule invading into the resin, to form a transparent calcium hydroxide. For this reason, this test is a test method which is more close to image of the actual sealing.

More specifically, with a progress of corrosion, the eroded portion becomes transparent calcium hydroxide. For this reason, the corner portion of the silver-white-colored metal calcium having a metallic luster is seen roundly. The corrosion degree in this test was evaluated by using a curvature radius R at the corner portion of the metal calcium, as shown in FIG. 5(b).

The un-corroded test specimen, in other words, the test specimen whose curvature radius R at the roundness of calcium due to corrosion, is 0 mm, was rated as "AA" (excellent). The corroded test specimen whose curvature radius R is more than 0 mm and less than 1 mm, was rated as "A" (good). The corroded test specimen whose curvature radius R is 1 mm or more and less than 5 mm, was rated as "C" (passed). The corroded test specimen whose curvature radius R is 5 mm or more, was rated as "D" (poor).

TABLE 2

| | | Composition | C. Ex. 1 | C. Ex. 2 | C. Ex. 3 | C. Ex. 4 | C. Ex. 5 | C. Ex. 6 | C. Ex. 7 | C. Ex. 8 | C. Ex. 9 |
|---|---|---|---|---|---|---|---|---|---|---|---|
| (a) | a-1 | GI-1000 (modified by AOI) | 30 | 30 | | | | | | 7 | 7 |
| | a-2 | GI-2000 (modified by AOI) | | | | | | | | | |
| | a-3 | GI-3000 (modified by AOI) | | | | | | | | | |
| | a-4 | HLBH-P 2000 (modified by AOI) | | | | | | | | | |
| | a-5 | HLBH-P 3000 (modified by AOI) | | | | | | | | | |
| | a-6 | GI-1000 (modified by MOI) | | | | | | | | | |
| | a-7 | CN307 | | | | | | | | | |
| | a-8 | CN308 | | | | | | | | | |
| | a-9 | CN9014 | | | | | | | | | |
| | a-10 | TE-2000 | | | | | | | | | |
| | a-11 | TEAI-1000 | | | | | 50 | | | | |
| | a-12 | EMA-3000 | | | | 79 | | | | | |
| | a-13 | Poly bdR-20LM Resin (modified by AOI) | | | | | | | 7 | | |
| | a-14 | LBH 10000 (modified by AOI) | | | | | | | | 7 | |
| | a-15 | BRENMER DA-800AU | | | | | | 10 | | | |
| (b) | b-1 | DCP-A | | | 69 | | | | | 89 | 89 |
| | b-2 | DCP | | | | | | | | | |
| | b-3 | 1,4-BDDA | | | | | | | | | |
| | b-4 | HDDA | | | | | | | | | |
| | b-5 | TCDDM (modified by AOI) | | | | | | | | | |
| | b-6 | Ethylene diacrylate | | | | | | | | | |
| | b-7 | Acrylic anhydride | | | | | | | | | 89 |
| | b-8 | Bis A (modified by AOI) | | | | | | | | 89 | |
| | b-9 | SR506 (isobornyl) | 39 | | | 49 | | | | | |
| | b-10 | Phenoxyethyl acrylate | | | | | 59 | | | | |
| (c) | c-1 | AlCH | 30 | | 20 | | | | | | |
| | c-2 | ALUMI-CHELATE M | | | | | | | | | |
| | c-3 | AlCH-TR | | | | | 30 | 3 | 3 | 3 | 3 |
| (d) | | ESACURE TZT | 1 | 1 | 1 | 1 | 1 | 1 | 1 | 1 | 1 |
| | | The mole number of (meth)acrylate groups (mol/100-g) | 0.22 | 0.49 | 0.05 | 0.29 | 0.35 | 0.60 | 0.59 | 0.36 | 1.42 |
| Evaluation | | Compatibility test (1 hr. after blended but before cured) | A | C | A | A | A | C | C | C | C |
| | | Compatibility test (24 hr. after blended but before cured) | A | A | A | A | A | A | A | A | C |
| | | Compatibility test (after cured) | A | A | A | A | A | A | A | A | A |
| | | Resin viscosity | A | A | D | D | A | D | D | D | A |
| | | Bendability test | A | A | AA | AA | D | A | A | A | D |
| | | Water vapor barrier property test (g/m²/24-hr) | 14 | 5 | 11 | 12 | 250 | 10 | 12 | 8 | 13 |
| | | Ca corrosion test | D | D | D | D | D | D | D | D | D |

Note:
"C. Ex." means Comparative Example.

| | | Composition | Ex. 1 | Ex. 2 | Ex. 3 | Ex. 4 |
|---|---|---|---|---|---|---|
| (a) | a-1 | GI-1000 (modified by AOI) | | 3 | 35 | 7 |
| | a-2 | GI-2000 (modified by AOI) | | | | |
| | a-3 | GI-3000 (modified by AOI) | | | | |
| | a-4 | HLBH-P 2000 (modified by AOI) | | | | |
| | a-5 | HLBH-P 3000 (modified by AOI) | | | | |
| | a-6 | GI-1000 (modified by MOI) | | | | |
| | a-7 | CN307 | | | | |
| | a-8 | CN308 | | | | |
| | a-9 | CN9014 | 7 | | | |
| | a-10 | TE-2000 | | | | |
| | a-11 | TEAI-1000 | | | | |
| | a-12 | EMA-3000 | | | | |
| | a-13 | Poly bdR-20LM Resin (modified by AOI) | | | | |
| | a-14 | LBH 10000 (modified by AOI) | | | | |
| | a-15 | BRENMER DA-800AU | | | | |
| (b) | b-1 | DCP-A | | 89 | 39 | 89 |
| | b-2 | DCP | | | | |
| | b-3 | 1,4-BDDA | | | | |
| | b-4 | HDDA | | | | |
| | b-5 | TCDDM (modified by AOI) | | | | |
| | b-6 | Ethylene diacrylate | 89 | | | |

TABLE 2-continued

|     |      |                                                           |      |      |      |      |
|-----|------|-----------------------------------------------------------|------|------|------|------|
|     | b-7  | Acrylic anhydride                                         |      |      |      |      |
|     | b-8  | Bis A (modified by AOI)                                   |      |      |      |      |
|     | b-9  | SR506 (isobornyl)                                         |      |      |      |      |
|     | b-10 | Phenoxyethyl acrylate                                     |      |      |      |      |
| (c) | c-1  | AlCH                                                      |      |      |      |      |
|     | c-2  | ALUMI-CHELATE M                                           |      |      |      |      |
|     | c-3  | AlCH-TR                                                   | 3    | 7    | 25   | 3    |
| (d) |      | ESACURE TZT                                               | 1    | 1    | 1    | 1    |
|     |      | The mole number of (meth)acrylate groups (mol/100-g)      | 1.05 | 0.59 | 0.30 | 0.59 |
| Evaluation | | Compatibility test (1 hr. after blended but before cured) | C | C | C | C |
|     |      | Compatibility test (24 hr. after blended but before cured) | A | A | A | A |
|     |      | Compatibility test (after cured)                          | A | A | A | A |
|     |      | Resin viscosity                                           | A | A | A | A |
|     |      | Bendability test                                          | AA | A | AA | A |
|     |      | Water vapor barrier property test (g/m²/24-hr)            | 2 | 2 | 5 | 2 |
|     |      | Ca corrosion test                                         | C | C | C | C |

Note:
"Ex." means Example according to this invention (the same will be applied in below).

TABLE 3

|     | Composition |                                | Ex. 5 | Ex. 6 | Ex. 7 | Ex. 8 | Ex. 9 | Ex. 10 | Ex. 11 |
|-----|------|--------------------------------------|-------|-------|-------|-------|-------|--------|--------|
| (a) | a-1  | GI-1000 (modified by AOI)            | 25    | 5     | 5     | 30    | 30    | 5      | 5      |
|     | a-2  | GI-2000 (modified by AOI)            |       |       |       |       |       |        |        |
|     | a-3  | GI-3000 (modified by AOI)            |       |       |       |       |       |        |        |
|     | a-4  | HLBH-P 2000 (modified by AOI)        |       |       |       |       |       |        |        |
|     | a-5  | HLBH-P 3000 (modified by AOI)        |       |       |       |       |       |        |        |
|     | a-6  | GI-1000 (modified by MOI)            |       |       |       |       |       |        |        |
|     | a-7  | CN307                                |       |       |       |       |       |        |        |
|     | a-8  | CN308                                |       |       |       |       |       |        |        |
|     | a-9  | CN9014                               |       |       |       |       |       |        |        |
|     | a-10 | TE-2000                              |       |       |       |       |       |        |        |
|     | a-11 | TEAI-1000                            |       |       |       |       |       |        |        |
|     | a-12 | EMA-3000                             |       |       |       |       |       |        |        |
|     | a-13 | Poly bdR-20LM Resin (modified by AOI) |      |       |       |       |       |        |        |
|     | a-14 | LBH 10000 (modified by AOI)          |       |       |       |       |       |        |        |
|     | a-15 | BRENMER DA-800AU                     |       |       |       |       |       |        |        |
| (b) | b-1  | DCP-A                                | 39    | 89    | 64    | 39    | 64    | 89     | 64     |
|     | b-2  | DCP                                  |       |       |       |       |       |        |        |
|     | b-3  | 1,4-BDDA                             |       |       |       |       |       |        |        |
|     | b-4  | HDDA                                 |       |       |       |       |       |        |        |
|     | b-5  | TCDDM (modified by AOI)              |       |       |       |       |       |        |        |
|     | b-6  | Ethylene diacrylate                  |       |       |       |       |       |        |        |
|     | b-7  | Acrylic anhydride                    |       |       |       |       |       |        |        |
|     | b-8  | Bis A (modified by AOI)              |       |       |       |       |       |        |        |
|     | b-9  | SR506 (isobornyl)                    |       |       |       |       |       |        |        |
|     | b-10 | Phenoxyethyl acrylate                |       |       |       |       |       |        |        |
| (c) | c-1  | AlCH                                 |       |       |       |       |       |        |        |
|     | c-2  | ALUMI-CHELATE M                      |       |       |       |       |       | 5      | 30     |
|     | c-3  | AlCH-TR                              | 35    | 5     | 30    | 30    | 5     |        |        |
| (d) |      | ESACURE TZT                          | 1     | 1     | 1     | 1     | 1     | 1      | 1      |
|     |      | The mole number of (meth)acrylate groups (mol/100-g) | 0.28 | 0.59 | 0.43 | 0.29 | 0.45 | 0.59 | 0.43 |
| Evaluation | | Compatibility test (1 hr. after blended but before cured) | C | A | A | A | A | A | A |
|     |      | Compatibility test (24 hr. after blended but before cured) | A | A | A | A | A | A | A |
|     |      | Compatibility test (after cured)     | A     | A     | A     | A     | A     | A      | A      |
|     |      | Resin viscosity                      | A     | AA    | AA    | AA    | AA    | AA     | AA     |
|     |      | Bendability test                     | AA    | A     | A     | AA    | AA    | A      | A      |
|     |      | Water vapor barrier property test (g/m²/24-hr) | 4 | 3 | 3 | 6 | 5 | 4 | 4 |
|     |      | Ca corrosion test                    | C     | A     | A     | A     | A     | AA     | AA     |

|     | Composition |                                | Ex. 12 | Ex. 13 | Ex. 14 | Ex. 15 | Ex. 16 | Ex. 17 | Ex. 18 |
|-----|------|--------------------------------------|--------|--------|--------|--------|--------|--------|--------|
| (a) | a-1  | GI-1000 (modified by AOI)            | 30     | 30     |        |        |        |        |        |
|     | a-2  | GI-2000 (modified by AOI)            |        |        | 15     |        |        |        |        |
|     | a-3  | GI-3000 (modified by AOI)            |        |        |        | 15     |        |        |        |
|     | a-4  | HLBH-P 2000 (modified by AOI)        |        |        |        |        | 15     |        |        |
|     | a-5  | HLBH-P 3000 (modified by AOI)        |        |        |        |        |        | 15     |        |
|     | a-6  | GI-1000 (modified by MOI)            |        |        |        |        |        |        | 15     |
|     | a-7  | CN307                                |        |        |        |        |        |        |        |
|     | a-8  | CN308                                |        |        |        |        |        |        |        |
|     | a-9  | CN9014                               |        |        |        |        |        |        |        |
|     | a-10 | TE-2000                              |        |        |        |        |        |        |        |
|     | a-11 | TEAI-1000                            |        |        |        |        |        |        |        |
|     | a-12 | EMA-3000                             |        |        |        |        |        |        |        |
|     | a-13 | Poly bdR-20LM Resin (modified by AOI) |       |        |        |        |        |        |        |
|     | a-14 | LBH 10000 (modified by AOI)          |        |        |        |        |        |        |        |

TABLE 3-continued

|   |      |                          |     |     |     |     |     |     |     |
|---|------|--------------------------|-----|-----|-----|-----|-----|-----|-----|
|   | a-15 | BRENMER DA-800AU         |     |     |     |     |     |     |     |
|(b)| b-1  | DCP-A                    | 39  | 64  | 64  | 64  | 64  | 64  | 64  |
|   | b-2  | DCP                      |     |     |     |     |     |     |     |
|   | b-3  | 1,4-BDDA                 |     |     |     |     |     |     |     |
|   | b-4  | HDDA                     |     |     |     |     |     |     |     |
|   | b-5  | TCDDM (modified by AOI)  |     |     |     |     |     |     |     |
|   | b-6  | Ethylene diacrylate      |     |     |     |     |     |     |     |
|   | b-7  | Acrylic anhydride        |     |     |     |     |     |     |     |
|   | b-8  | Bis A (modified by AOI)  |     |     |     |     |     |     |     |
|   | b-9  | SR506 (isobornyl)        |     |     |     |     |     |     |     |
|   | b-10 | Phenoxyethyl acrylate    |     |     |     |     |     |     |     |
|(c)| c-1  | AlCH                     |     |     |     |     |     |     |     |
|   | c-2  | ALUMI-CHELATE M          | 30  | 5   | 20  | 20  | 20  | 20  | 20  |
|   | c-3  | AlCH-TR                  |     |     |     |     |     |     |     |
|(d)|      | ESACURE TZT              | 1   | 1   | 1   | 1   | 1   | 1   | 1   |
|   |      | The mole number of (meth)acrylate groups (mol/100-g) | 0.29 | 0.45 | 0.43 | 0.43 | 0.43 | 0.43 | 0.44 |
| Evaluation |      | Compatibility test (1 hr. after blended but before cured) | A | A | A | A | A | A | A |
|   |      | Compatibility test (24 hr. after blended but before cured) | A | A | A | A | A | A | A |
|   |      | Compatibility test (after cured) | A | A | A | A | A | A | A |
|   |      | Resin viscosity          | AA  | AA  | AA  | A   | AA  | A   | AA  |
|   |      | Bendability test         | AA  | AA  | AA  | AA  | AA  | AA  | AA  |
|   |      | Water vapor barrier property test (g/m$^2$/24-hr) | 5 | 5 | 4 | 4 | 3 | 3 | 4 |
|   |      | Ca corrosion test        | AA  | AA  | AA  | AA  | AA  | AA  | AA  |

TABLE 4

|   | Composition |                          | Ex. 19 | Ex. 20 | Ex. 21 | Ex. 22 | Ex. 23 | Ex. 24 |
|---|------|--------------------------|--------|--------|--------|--------|--------|--------|
|(a)| a-1  | GI-1000 (modified by AOI) |       |        |        |        |        |        |
|   | a-2  | GI-2000 (modified by AOI) |       |        |        |        |        |        |
|   | a-3  | GI-3000 (modified by AOI) |       |        |        |        |        |        |
|   | a-4  | HLBH-P 2000 (modified by AOI) |   |        |        |        |        |        |
|   | a-5  | HLBH-P 3000 (modified by AOI) |   |        |        |        |        |        |
|   | a-6  | GI-1000 (modified by MOI) |       |        |        |        |        |        |
|   | a-7  | CN307                    | 15     |        |        |        |        |        |
|   | a-8  | CN308                    |        | 15     |        |        |        |        |
|   | a-9  | CN9014                   |        |        | 15     |        |        |        |
|   | a-10 | TE-2000                  |        |        |        | 15     |        |        |
|   | a-11 | TEAI-1000                |        |        |        |        | 15     |        |
|   | a-12 | EMA-3000                 |        |        |        |        |        | 15     |
|   | a-13 | Poly bdR-20LM Resin (modified by AOI) |  |    |        |        |        |        |
|   | a-14 | LBH 10000 (modified by AOI) |     |        |        |        |        |        |
|   | a-15 | BRENMER DA-800AU         |        |        |        |        |        |        |
|(b)| b-1  | DCP-A                    | 64     | 64     | 64     | 64     | 64     | 64     |
|   | b-2  | DCP                      |        |        |        |        |        |        |
|   | b-3  | 1,4-BDDA                 |        |        |        |        |        |        |
|   | b-4  | HDDA                     |        |        |        |        |        |        |
|   | b-5  | TCDDM (modified by AOI)  |        |        |        |        |        |        |
|   | b-6  | Ethylene diacrylate      |        |        |        |        |        |        |
|   | b-7  | Acrylic anhydride        |        |        |        |        |        |        |
|   | b-8  | Bis A (modified by AOI)  |        |        |        |        |        |        |
|   | b-9  | SR506 (isobornyl)        |        |        |        |        |        |        |
|   | b-10 | Phenoxyethyl acrylate    |        |        |        |        |        |        |
|(c)| c-1  | AlCH                     |        |        |        |        |        |        |
|   | c-2  | ALUMI-CHELATE M          | 20     | 20     | 20     | 20     | 20     | 20     |
|   | c-3  | AlCH-TR                  |        |        |        |        |        |        |
|(d)|      | ESACURE TZT              | 1      | 1      | 1      | 1      | 1      | 1      |
|   |      | The mole number of (meth)acrylate groups (mol/100-g) | 0.43 | 0.43 | 0.43 | 0.43 | 0.44 | 0.43 |
| Evaluation |  | Compatibility test (1 hr. after blended but before cured) | A | A | A | A | A | A |
|   |      | Compatibility test (24 hr. after blended but before cured) | A | A | A | A | A | A |
|   |      | Compatibility test (after cured) | A | A | A | A | A | A |
|   |      | Resin viscosity          | AA     | AA     | AA     | AA     | A      | A      |
|   |      | Bendability test         | AA     | AA     | AA     | AA     | AA     | AA     |
|   |      | Water vapor barrier property test (g/m$^2$/24-hr) | 7 | 3 | 3 | 6 | 3 | 4 |
|   |      | Ca corrosion test        | AA     | AA     | AA     | AA     | AA     | AA     |
|   | Composition |                       | Ex. 25 | Ex. 26 | Ex. 27 | Ex. 28 | Ex. 29 |        |
|(a)| a-1  | GI-1000 (modified by AOI) | 15   | 15     | 15     | 15     | 15     |        |
|   | a-2  | GI-2000 (modified by AOI) |      |        |        |        |        |        |
|   | a-3  | GI-3000 (modified by AOI) |      |        |        |        |        |        |
|   | a-4  | HLBH-P 2000 (modified by AOI) |  |        |        |        |        |        |
|   | a-5  | HLBH-P 3000 (modified by AOI) |  |        |        |        |        |        |
|   | a-6  | GI-1000 (modified by MOI) |      |        |        |        |        |        |
|   | a-7  | CN307                    |        |        |        |        |        |        |
|   | a-8  | CN308                    |        |        |        |        |        |        |
|   | a-9  | CN9014                   |        |        |        |        |        |        |

TABLE 4-continued

|  |  |  |  |  |  |  |  |
|---|---|---|---|---|---|---|---|
|  | a-10 | TE-2000 |  |  |  |  |  |
|  | a-11 | TEAI-1000 |  |  |  |  |  |
|  | a-12 | EMA-3000 |  |  |  |  |  |
|  | a-13 | Poly bdR-20LM Resin (modified by AOI) |  |  |  |  |  |
|  | a-14 | LBH 10000 (modified by AOI) |  |  |  |  |  |
|  | a-15 | BRENMER DA-800AU |  |  |  |  |  |
| (b) | b-1 | DCP-A |  |  |  |  |  |
|  | b-2 | DCP | 64 |  |  |  |  |
|  | b-3 | 1,4-BDDA |  | 64 |  |  |  |
|  | b-4 | HDDA |  |  | 64 |  |  |
|  | b-5 | TCDDM (modified by AOI) |  |  |  | 64 |  |
|  | b-6 | Ethylene diacrylate |  |  |  |  | 64 |
|  | b-7 | Acrylic anhydride |  |  |  |  |  |
|  | b-8 | Bis A (modified by AOI) |  |  |  |  |  |
|  | b-9 | SR506 (isobornyl) |  |  |  |  |  |
|  | b-10 | Phenoxyethyl acrylate |  |  |  |  |  |
| (c) | c-1 | AlCH |  |  |  |  |  |
|  | c-2 | ALUMI-CHELATE M | 20 | 20 | 20 | 20 | 20 |
|  | c-3 | AlCH-TR |  |  |  |  |  |
| (d) |  | ESACURE TZT | 1 | 1 | 1 | 1 | 1 |
|  | The mole number of (meth)acrylate groups (mol/100-g) |  | 0.40 | 0.66 | 0.58 | 0.28 | 0.77 |
| Evaluation | Compatibility test (1 hr. after blended but before cured) |  | A | A | A | A | A |
|  | Compatibility test (24 hr. after blended but before cured) |  | A | A | A | A | A |
|  | Compatibility test (after cured) |  | A | A | A | A | A |
|  | Resin viscosity |  | AA | AA | AA | AA | AA |
|  | Bendability test |  | AA | AA | AA | AA | AA |
|  | Water vapor barrier property test (g/m$^2$/24-hr) |  | 5 | 3 | 4 | 4 | 3 |
|  | Ca corrosion test |  | AA | AA | AA | AA | AA |

Note that, the materials used for the sealing resin compositions are as follows.

Low molecular weight (meth)acrylate (b)
LIGHT ACRYLATE DCP-A (manufactured by Kyoeisha Chemical Co., Ltd., dimethylol-tricyclodecane diacrylate, molecular weight 304) DCP (Shin-Nakamura Chemical Co., Ltd., tricyclodecane dimethanol dimethacrylate, molecular weight 332)
VISCOAT #195, 1,4-BDDA (manufactured by Osaka Organic Chemical Industry Ltd., 1,4-butanediol diacrylate, molecular weight 198)
VISCOAT #230, HDDA (manufactured by Osaka Organic Chemical Industry Ltd., 1,6-hexanediol diacrylate, molecular weight 226)
TCDDM (modified by AOI) (molecular weight 478, the number of acryloyl groups 2.0)
Any of the following materials was prepared in the same manner as in the above-described preparation of the acylate oligomer (a-1), except for using 20 g of tricyclodecane dimethanol (abbreviation TCDDM, manufactured by Tokyo Chemical Industry Co., Ltd., molecular weight 196.3) and 28.8 g of KARENZ AOI (manufactured by Showa Denko K.K., 2-isocyanatoethyl acrylate, molecular weight 141.1).
Ethylene diacrylate (manufactured by Wako Pure Chemical Industries, Ltd., molecular weight 170)
Acrylic acid anhydride (manufactured by Kyoeisha Chemical Co., Ltd., molecular weight 126)
BisA (modified by AOI) (molecular weight 508, the number of acryloyl groups 2.0)
Any of the following materials was prepared in the same manner as in the above-described preparation of the acylate oligomer (a-1), except for using 20 g of bisphenol A (manufactured by Tokyo Chemical Industry Co., Ltd., molecular weight 228.3) and 25.0 g of KARENZ AOI (manufactured by Showa Denko K.K., 2-isocyanatoethyl acrylate, molecular weight 141.1).
SR506 (manufactured by SARTOMER Inc., isobornyl acrylate, molecular weight 208)
VISCOAT#192, PEA (manufactured by Osaka Organic Chemical Industry Ltd., phenoxyethyl acrylate, molecular weight 180) (described as "phenoxyethyl acrylate" in Tables 2 to 4)

Moisture-Reactive Organometallic Compound (c)
ALCH (manufactured by Kawaken Fine Chemicals Co., Ltd., aluminum ethylacetoacetate diisopropylate)
ALCH-TR (manufactured by Kawaken Fine Chemicals Co., Ltd., aluminum trisethylacetoacetate)
ALUMI-CHELATE M (manufactured by Kawaken Fine Chemicals Co., Ltd., aluminum alkylacetoacetate diisopropylate)
ALUMINUM ETHOXIDE (manufactured by Kawaken Fine Chemicals Co., Ltd., aluminum ethylate)
Polymerization Initiator (d)
ESACURE TZT (manufactured by DKSH, a mixture of 2,4,6-trimethyl benzophenone and benzophenone)

As is shown in Tables 2 to 4, it was found that, in each of Examples 1 to 29, a good evaluation was obtained in terms of both Ca corrosion test and water vapor barrier property test, and the cured film of the sealing resin composition of the present invention had a high water vapor barrier property. Further, any of the resin viscosities was low enough to do the sealing working. In addition, it was found that any of the cured films was excellent in bendability, and was able to sufficiently work as a sealant, by bending so that the sealant moves on with the substrate, even in the sealing of a resin film having bendability or an ultrathin glass film.

To the contrary, in each of Comparative Examples 1 to 9, each of which does not have a low molecular weight (meth)acrylate or a moisture-reactive organometallic compound, or does not satisfy the range of the present invention with respect to the number of (meth)acryloyl groups or the molecular weight of the low molecular weight (meth)acrylate or the (meth)acrylate oligomer, there was progression of metal calcium corrosion. In addition, in Comparative Examples 1, and 3 to 9, at least one of resin viscosity, bendability, and water vapor barrier property was insufficient.

Having described our invention as related to the present embodiments, it is our intention that the invention not be limited by any of the details of the description, unless otherwise specified, but rather be construed broadly within its spirit and scope as set out in the accompanying claims.

This application claims priority on Patent Application No. 2015-017221 filed in Japan on Jan. 30, 2015, which is entirely herein incorporated by reference.

REFERENCE SIGNS LIST

1 Sealing substrate
2 Sealing resin
3 Organic light-emitting diode element
4 Element substrate
b Spacer (filler)
5, 5A Organic light-emitting device (image display device)
10 Sidewall sealant (adhesive, glass frit, or the like)
11 Sealing substrate
12 Sealing resin
13 Organic light-emitting diode element
14 Element substrate
15 Organic light-emitting device (image display device)
21 Inorganic thin film
22 Organic thin film (sealing resin)
23 Organic light-emitting diode element
24 Element substrate
25 Organic light-emitting device (image display device)
51 Sealing resin
52 Metal calcium
53 Ca specimen
54 Corroded metal calcium
55 Ca specimen after test
R Curvature radius

The invention claimed is:

1. A curable and hygroscopic resin composition for sealing electronic devices, comprising
from 5 to 30 mass % of at least a (meth)acrylate oligomer (a) having a number-average molecular weight of 1,500 to 5,000,
from 40 to 90 mass % of a low molecular weight (meth)acrylate (b) having an average molecular weight of 170 to 500,
from 5 to 30 mass % of a moisture-reactive organometallic compound (c), and
a polymerization initiator (d),
wherein the (meth)acrylate oligomer (a) and the low molecular weight (meth)acrylate (b) are multifunctional (meth)acrylates in which the number of (meth)acryloyl groups is from 1.5 to 3 in one molecule of each of the (meth)acrylate oligomer (a) and the low molecular weight (meth)acrylate (b); and
wherein the (meth)acrylate oligomer (a) is a resin whose main chain is a polybutadiene or a hydrogenated polybutadiene.

2. The curable and hygroscopic resin composition for sealing electronic devices as claimed in claim 1, wherein a moisture permeability of a cured film having a thickness of 100 μm, which has been formed by curing a composition in which the moisture-reactive organometallic compound (c) is removed from the curable and hygroscopic resin composition for sealing electronic devices, is 10 $g/m^2$/24-hr or less under the condition of 40° C. and 90% relative humidity.

3. The curable and hygroscopic resin composition for sealing electronic devices as claimed in claim 1, wherein the moisture-reactive organometallic compound (c) has at least one ligand having an acetylacetonato coordinating group and at least one alkoxide ligand.

4. A sealing resin, formed by shaping the curable and hygroscopic resin composition for sealing electronic devices as claimed in claim 1 into a film, and curing the film.

5. An electronic device, having the sealing resin as claimed in claim 4.

6. An electronic device, sealed with the curable and hygroscopic resin composition for sealing electronic devices as claimed in claim 1.

* * * * *